United States Patent
Kessler et al.

(10) Patent No.: US 10,368,902 B2
(45) Date of Patent: **\*Aug. 6, 2019**

(54) TISSUE-REMOVING CATHETER INCLUDING OPERATIONAL CONTROL MECHANISM

(71) Applicant: Covidien LP, Mansfield, MA (US)

(72) Inventors: Jason Kessler, Minneapolis, MN (US); Benjamin Fruland, Blaine, MN (US); Bryan Ladd, Minneapolis, MN (US); Cassandra Nigh, Andover, MN (US)

(73) Assignee: Covidien LP, Mansfield, MA (US)

( \* ) Notice: Subject to any disclaimer, the term of this patent is extended or adjusted under 35 U.S.C. 154(b) by 354 days.

This patent is subject to a terminal disclaimer.

(21) Appl. No.: 15/425,095

(22) Filed: Feb. 6, 2017

(65) Prior Publication Data

US 2017/0143373 A1    May 25, 2017

Related U.S. Application Data

(63) Continuation of application No. 14/074,767, filed on Nov. 8, 2013, now Pat. No. 9,597,110.
(Continued)

(51) Int. Cl.
*A61B 17/3207* (2006.01)
*A61B 17/00* (2006.01)

(52) U.S. Cl.
CPC ........... *A61B 17/320783* (2013.01); *A61B 17/320758* (2013.01); *A61B 2017/00022* (2013.01);
(Continued)

(58) Field of Classification Search
CPC ...... A61B 17/32075; A61B 17/320758; A61B 17/320783; A61B 2017/00022;
(Continued)

(56) References Cited

U.S. PATENT DOCUMENTS

| | | |
|---|---|---|
| 1,481,078 A | 1/1924 | Albertson |
| 2,701,559 A | 2/1955 | Cooper |

(Continued)

FOREIGN PATENT DOCUMENTS

| | | |
|---|---|---|
| CA | 2000621 A1 | 4/1990 |
| EP | 0086048 A2 | 8/1983 |

(Continued)

OTHER PUBLICATIONS

Schroeder, Current Sensing Using Resistors, Mar. 5, 2015, ECN Magazine.

*Primary Examiner* — Elizabeth Houston
*Assistant Examiner* — Kankindi Rwego

(57) ABSTRACT

A tissue-removing catheter includes a sensor configured to detect a parameter of the catheter during the cutting operation of the catheter when a tissue-removing element is in a tissue-removing position. A locking control circuit is in electrical communication with the sensor and a locking device. During an operational control function, the locking control circuit receives a signal from the sensor based at least in part on the parameter of the catheter detected during the cutting operation of the catheter. The locking control circuit determines whether the received signal is indicative of a tissue-removing element engaging a non-tissue obstruction. The locking control circuit configures the locking device in its locked configuration to inhibit movement of the tissue-removing element from its tissue-removing position to its neutral position if the received signal is indicative of the tissue-removing element engaging a non-tissue obstruction.

20 Claims, 34 Drawing Sheets

Related U.S. Application Data

(60) Provisional application No. 61/723,892, filed on Nov. 8, 2012.

(52) U.S. Cl.
CPC ............... *A61B 2017/00075* (2013.01); *A61B 2017/00123* (2013.01); *A61B 2017/320791* (2013.01)

(58) Field of Classification Search
CPC ........... A61B 2017/00075; A61B 2017/00123; A61B 2017/00367; A61B 2017/00371; A61B 2017/00376; A61B 2017/0038; A61B 2017/00384; A61B 2017/00389; A61B 2017/00393; A61B 2017/00398; A61B 2017/00402; A61B 2017/00407; A61B 2017/00411; A61B 2014/00415; A61B 2017/320791
See application file for complete search history.

(56) References Cited

U.S. PATENT DOCUMENTS

| | | |
|---|---|---|
| 2,850,007 A | 9/1958 | Lingley |
| 3,064,651 A | 11/1962 | Henderson |
| 3,082,805 A | 3/1963 | Royce |
| 3,614,953 A | 10/1971 | Moss |
| 3,683,891 A | 8/1972 | Eskridge et al. |
| 3,732,858 A | 5/1973 | Banko |
| 3,749,085 A | 7/1973 | Willson et al. |
| 3,800,783 A | 4/1974 | Jamshidi |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 4,007,732 A | 2/1977 | Kvavle et al. |
| 4,020,847 A | 5/1977 | Clark, III |
| 4,030,503 A | 6/1977 | Clark, III |
| 4,038,985 A | 8/1977 | Chiulli |
| 4,112,708 A | 9/1978 | Fukuda |
| 4,177,797 A | 12/1979 | Baylis et al. |
| 4,273,128 A | 6/1981 | Lary |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,667 A | 9/1987 | Masch |
| 4,705,038 A | 11/1987 | Sjostrom et al. |
| 4,706,671 A | 11/1987 | Weinrib |
| 4,728,319 A | 3/1988 | Masch |
| 4,729,763 A | 3/1988 | Henrie |
| 4,732,154 A | 3/1988 | Shiber |
| 4,745,919 A | 5/1988 | Bundy et al. |
| 4,747,406 A | 5/1988 | Nash |
| 4,747,821 A | 5/1988 | Kensey et al. |
| 4,754,755 A | 7/1988 | Husted |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,819,634 A | 4/1989 | Shiber |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,490 A | 12/1989 | Shiber |
| 4,887,613 A | 12/1989 | Farr et al. |
| 4,894,051 A | 1/1990 | Shiber |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,950,238 A | 8/1990 | Sullivan |
| 4,957,482 A | 9/1990 | Shiber |
| 4,966,604 A | 10/1990 | Reiss |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,026,384 A | 6/1991 | Farr et al. |
| 5,030,201 A | 7/1991 | Palestrant |
| 5,047,040 A | 9/1991 | Simpson et al. |
| 5,049,124 A | 9/1991 | Bales, Jr. |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause |
| 5,078,722 A | 1/1992 | Stevens |
| 5,078,723 A | 1/1992 | Dance et al. |
| 5,087,265 A | 2/1992 | Summers |
| 5,092,839 A | 3/1992 | Kipperman |
| 5,092,873 A | 3/1992 | Simpson et al. |
| 5,100,426 A | 3/1992 | Nixon |
| 5,112,345 A | 5/1992 | Farr |
| 5,114,399 A | 5/1992 | Kovalcheck |
| 5,135,531 A | 8/1992 | Shiber |
| 5,154,705 A | 10/1992 | Fleischhacker et al. |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,192,291 A | 3/1993 | Pannek, Jr. |
| 5,195,956 A | 3/1993 | Stockmeier |
| 5,222,966 A | 6/1993 | Perkins et al. |
| 5,224,945 A | 7/1993 | Pannek, Jr. |
| 5,242,460 A | 9/1993 | Klein et al. |
| 5,242,461 A | 9/1993 | Kortenbach et al. |
| 5,263,959 A | 11/1993 | Fischell |
| 5,267,955 A | 12/1993 | Hanson |
| 5,269,793 A | 12/1993 | Simpson |
| 5,273,526 A | 12/1993 | Dance et al. |
| 5,284,486 A | 2/1994 | Kotula et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,314,438 A | 5/1994 | Shturman |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance |
| 5,366,463 A | 11/1994 | Ryan |
| 5,370,609 A | 12/1994 | Drasler et al. |

(56) References Cited

U.S. PATENT DOCUMENTS

| | | | |
|---|---|---|---|
| 5,370,651 A | 12/1994 | Summers | |
| 5,372,601 A | 12/1994 | Lary | |
| 5,373,619 A | 12/1994 | Fleischhacker et al. | |
| 5,378,234 A | 1/1995 | Hammerslag et al. | |
| 5,395,311 A | 3/1995 | Andrews | |
| 5,395,335 A | 3/1995 | Jang | |
| 5,397,345 A | 3/1995 | Lazarus | |
| 5,403,334 A | 4/1995 | Evans et al. | |
| 5,409,454 A | 4/1995 | Fischell et al. | |
| 5,423,740 A | 6/1995 | Sullivan et al. | |
| 5,423,799 A | 6/1995 | Shiu | |
| 5,423,846 A | 6/1995 | Fischell | |
| 5,431,673 A | 7/1995 | Summers et al. | |
| 5,441,510 A | 8/1995 | Simpson et al. | |
| 5,443,497 A | 8/1995 | Venbrux | |
| 5,454,809 A | 10/1995 | Janssen | |
| 5,489,295 A | 2/1996 | Piplani et al. | |
| 5,501,694 A | 3/1996 | Ressemann et al. | |
| 5,507,292 A | 4/1996 | Jang et al. | |
| 5,507,760 A | 4/1996 | Wynne et al. | |
| 5,507,761 A | 4/1996 | Duer | |
| 5,512,044 A | 4/1996 | Duer | |
| 5,514,115 A | 5/1996 | Frantzen et al. | |
| 5,522,825 A | 6/1996 | Kropf et al. | |
| 5,522,880 A | 6/1996 | Barone et al. | |
| 5,531,690 A | 7/1996 | Solar | |
| 5,554,163 A | 9/1996 | Shturman | |
| 5,556,408 A | 9/1996 | Farhat | |
| 5,562,726 A | 10/1996 | Chuter | |
| 5,562,728 A | 10/1996 | Lazarus et al. | |
| 5,569,275 A | 10/1996 | Kotula et al. | |
| 5,569,276 A | 10/1996 | Jang et al. | |
| 5,569,277 A | 10/1996 | Evans et al. | |
| 5,569,279 A | 10/1996 | Rainin | |
| 5,571,130 A | 11/1996 | Simpson et al. | |
| 5,575,817 A | 11/1996 | Martin | |
| 5,584,843 A | 12/1996 | Wulfman et al. | |
| 5,602,449 A * | 2/1997 | Krause | A61B 17/32002 318/400.09 |
| 5,609,605 A | 3/1997 | Marshall et al. | |
| 5,624,457 A | 4/1997 | Farley et al. | |
| 5,626,576 A | 5/1997 | Janssen | |
| 5,628,761 A | 5/1997 | Rizik | |
| 5,632,754 A | 5/1997 | Farley et al. | |
| 5,632,755 A | 5/1997 | Nordgren et al. | |
| 5,643,296 A | 7/1997 | Hundertmark et al. | |
| 5,649,941 A | 7/1997 | Lary | |
| 5,662,671 A | 9/1997 | Barbut et al. | |
| 5,665,098 A | 9/1997 | Kelly et al. | |
| 5,669,920 A | 9/1997 | Conley et al. | |
| 5,676,696 A | 10/1997 | Marcade | |
| 5,676,697 A | 10/1997 | McDonald | |
| 5,681,336 A | 10/1997 | Clement et al. | |
| 5,683,449 A | 11/1997 | Marcade | |
| 5,683,453 A | 11/1997 | Palmaz | |
| 5,695,506 A | 12/1997 | Pike et al. | |
| 5,695,507 A | 12/1997 | Auth et al. | |
| 5,697,944 A | 12/1997 | Lary | |
| 5,700,240 A | 12/1997 | Barwick, Jr. et al. | |
| 5,707,350 A | 1/1998 | Krause et al. | |
| 5,707,383 A | 1/1998 | Bays et al. | |
| 5,713,913 A | 2/1998 | Lary et al. | |
| 5,728,123 A | 3/1998 | Lemelson et al. | |
| 5,733,296 A | 3/1998 | Rogers et al. | |
| 5,735,816 A | 4/1998 | Lieber et al. | |
| 5,766,192 A | 6/1998 | Zacca | |
| 5,772,674 A | 6/1998 | Nakhjavan | |
| 5,776,153 A | 7/1998 | Rees | |
| 5,779,673 A | 7/1998 | Roth et al. | |
| 5,779,721 A | 7/1998 | Nash | |
| 5,779,722 A | 7/1998 | Shturman et al. | |
| 5,792,157 A | 8/1998 | Mische et al. | |
| 5,797,949 A | 8/1998 | Parodi | |
| 5,807,329 A | 9/1998 | Gelman | |
| 5,820,592 A | 10/1998 | Hammerslag | |
| 5,824,039 A | 10/1998 | Piplani et al. | |
| 5,824,055 A | 10/1998 | Spiridigliozzi et al. | |
| 5,827,229 A | 10/1998 | Auth et al. | |
| 5,827,304 A | 10/1998 | Hart | |
| 5,827,322 A | 10/1998 | Williams | |
| 5,836,957 A | 11/1998 | Schulz et al. | |
| 5,843,022 A | 12/1998 | Willard et al. | |
| 5,843,103 A | 12/1998 | Wulfman | |
| 5,843,161 A | 12/1998 | Solovay | |
| 5,871,536 A | 2/1999 | Lazarus | |
| 5,873,882 A | 2/1999 | Straub et al. | |
| 5,876,414 A | 3/1999 | Straub | |
| 5,938,645 A | 8/1999 | Gordon | |
| 5,938,672 A | 8/1999 | Nash | |
| 5,941,869 A | 8/1999 | Patterson et al. | |
| 6,001,112 A | 12/1999 | Taylor | |
| 6,032,673 A | 3/2000 | Savage et al. | |
| 6,095,990 A | 8/2000 | Parodi | |
| 6,152,909 A | 11/2000 | Bagaoisan et al. | |
| 6,156,046 A | 12/2000 | Passafaro et al. | |
| 6,159,195 A | 12/2000 | Ha et al. | |
| 6,208,898 B1 | 3/2001 | Gliner et al. | |
| 6,238,405 B1 | 5/2001 | Findlay, III et al. | |
| 6,245,084 B1 * | 6/2001 | Mark | A61B 17/32002 606/167 |
| 6,312,444 B1 | 11/2001 | Barbut | |
| 6,451,036 B1 | 9/2002 | Heitzmann et al. | |
| 6,454,779 B1 | 9/2002 | Taylor | |
| 6,482,217 B1 | 11/2002 | Pintor et al. | |
| 6,623,437 B2 | 9/2003 | Hinchliffe et al. | |
| 6,623,495 B2 | 9/2003 | Findlay, III et al. | |
| 6,652,505 B1 | 11/2003 | Tsugita | |
| 6,656,195 B2 | 12/2003 | Peters et al. | |
| 6,666,874 B2 | 12/2003 | Heitzmann et al. | |
| 6,790,204 B2 | 9/2004 | Ladno-Azizi et al. | |
| 6,790,215 B2 | 9/2004 | Findlay, III et al. | |
| 6,843,797 B2 | 1/2005 | Nash et al. | |
| 6,849,068 B1 | 2/2005 | Bagaoisan, Jr. et al. | |
| 6,969,384 B2 | 11/2005 | de Juan, Jr. et al. | |
| 7,172,610 B2 | 2/2007 | Heitzmann et al. | |
| 7,235,088 B2 | 6/2007 | Pintor et al. | |
| 7,479,147 B2 | 1/2009 | Honetcutt et al. | |
| 7,771,445 B2 | 8/2010 | Heitzmann et al. | |
| 9,597,110 B2 * | 3/2017 | Kessler | A61B 17/32075 |
| 2001/0044622 A1 | 11/2001 | Vardi et al. | |
| 2002/0058904 A1 | 5/2002 | Boock et al. | |
| 2002/0095141 A1 | 7/2002 | Belef et al. | |
| 2002/0177800 A1 | 11/2002 | Bagaoisan et al. | |
| 2002/0188307 A1 | 12/2002 | Pintor et al. | |
| 2003/0023263 A1 | 1/2003 | Krolik et al. | |
| 2003/0120295 A1 | 6/2003 | Simpson et al. | |
| 2003/0229369 A1 | 12/2003 | Findlay, III et al. | |
| 2004/0049225 A1 | 3/2004 | Denison | |
| 2004/0087988 A1 | 5/2004 | Heitzmann et al. | |
| 2005/0004594 A1 | 1/2005 | Nool et al. | |
| 2006/0259052 A1 | 11/2006 | Pintor et al. | |

FOREIGN PATENT DOCUMENTS

| | | |
|---|---|---|
| EP | 0291170 A1 | 11/1988 |
| EP | 0373927 A2 | 6/1990 |
| EP | 0448859 A2 | 10/1991 |
| EP | 0463798 A1 | 1/1992 |
| EP | 0514810 A1 | 11/1992 |
| EP | 0533320 A2 | 3/1993 |
| EP | 0657140 A1 | 6/1995 |
| GB | 2093353 A | 9/1982 |
| GB | 2210965 A | 6/1989 |
| WO | 8906517 A1 | 7/1989 |
| WO | 9313716 A1 | 7/1993 |
| WO | 9313717 A1 | 7/1993 |
| WO | 9521576 A1 | 8/1995 |
| WO | 9611648 A1 | 4/1996 |
| WO | 9746164 A1 | 12/1997 |
| WO | 9804199 A1 | 2/1998 |
| WO | 9824372 A1 | 6/1998 |
| WO | 9952454 A1 | 10/1999 |

(56) References Cited

FOREIGN PATENT DOCUMENTS

| WO | 0130433 A1 | 5/2001 |
|---|---|---|
| WO | 0143809 A1 | 6/2001 |

* cited by examiner

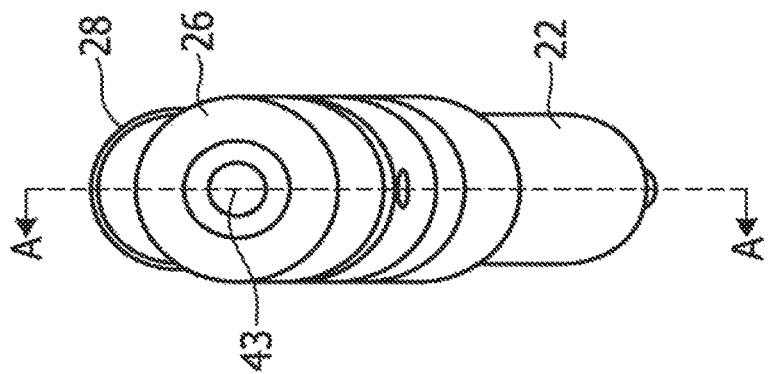
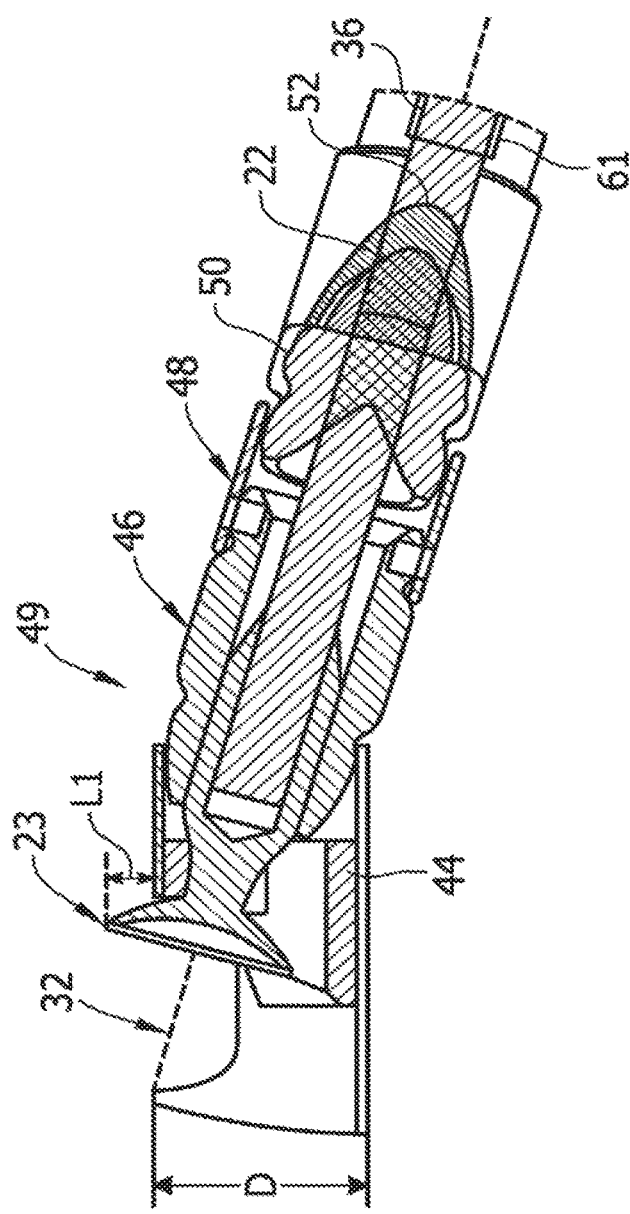
FIG. 4A
FIG. 4B

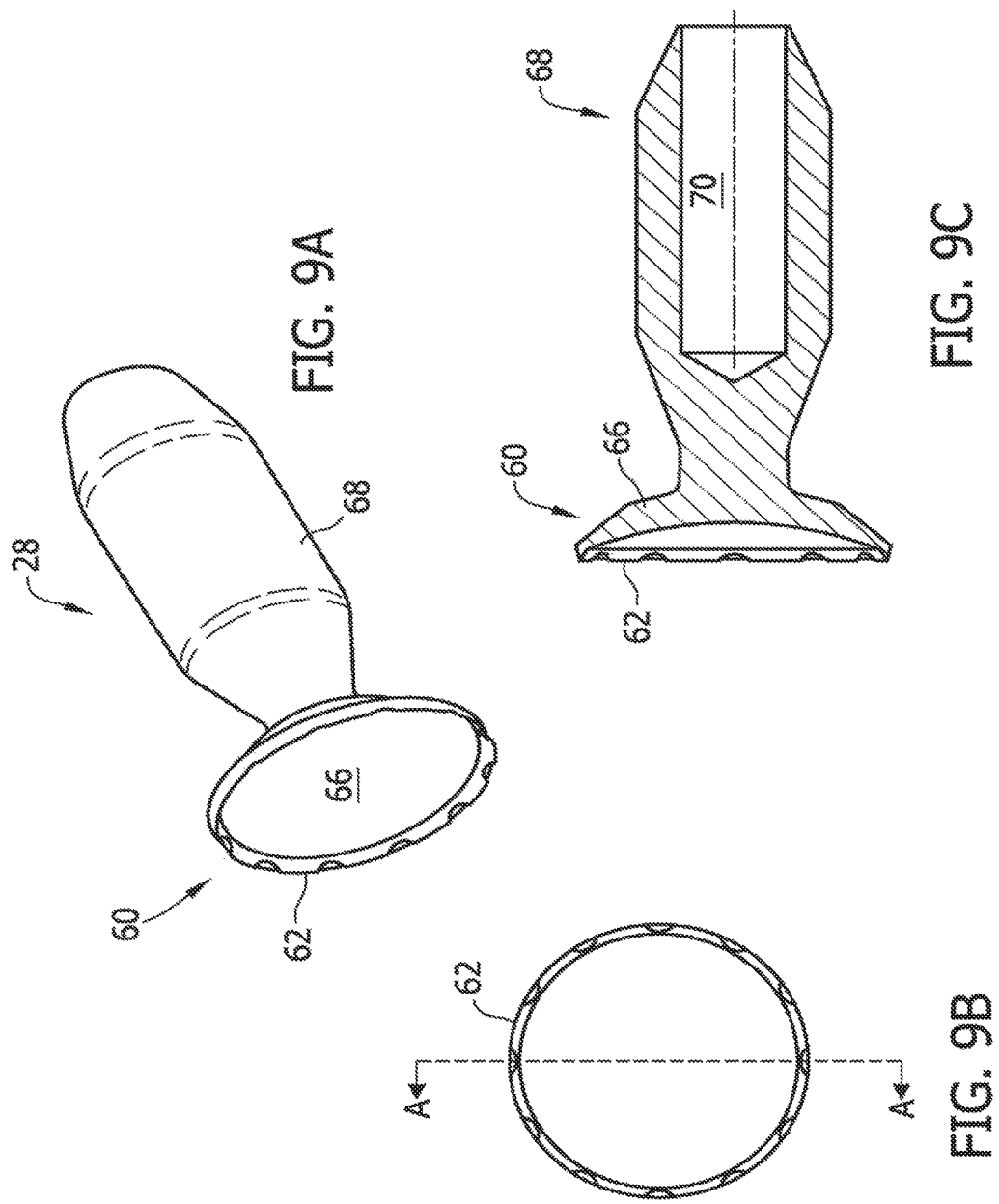

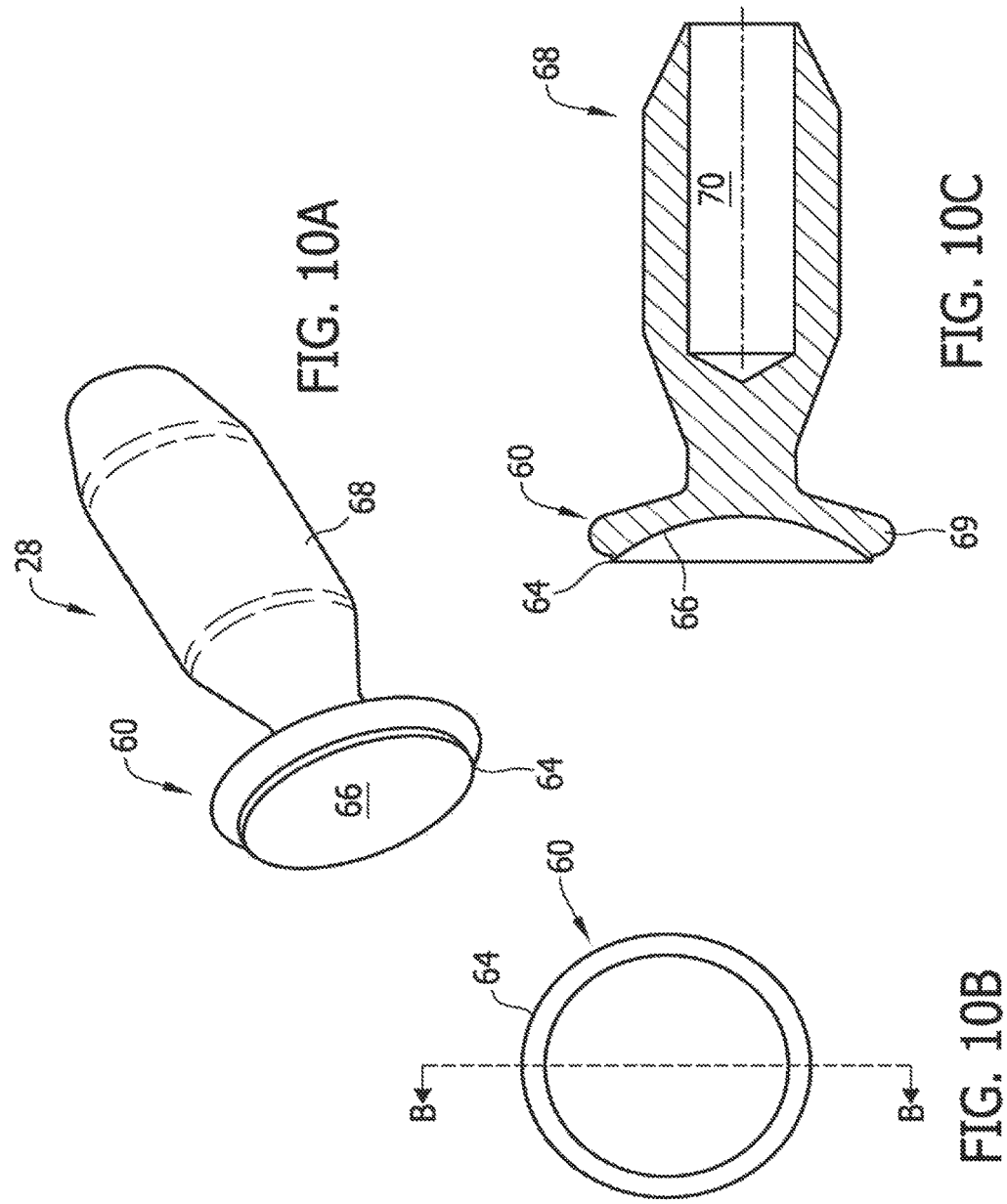

TISSUE-REMOVING CATHETER INCLUDING OPERATIONAL CONTROL MECHANISM

CROSS-REFERENCE TO RELATED APPLICATIONS

The present application is a Continuation of and claims priority to U.S. patent application Ser. No. 14/074,767, filed Nov. 8, 2013, now allowed, which claims priority to U.S. Provisional Application Ser. No. 61/723,892, filed Nov. 8, 2012, the entirety of which is hereby incorporated by reference.

FIELD OF THE DISCLOSURE

Aspects of the present invention generally relate to a tissue-removing catheter for removing tissue from a body lumen including an operational control mechanism.

BACKGROUND

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

Although atherectomy catheters have proven very successful in treating atherosclerosis, problems may arise when using atherectomy catheters to treat in-stent restenosis. When using many atherectomy catheters, including currently available side-cutting catheters, to treat in-stent restenosis, the stent may become entangled with the rotating cutter and/or cutter driveshaft. Such entanglement may lead to stent malapposition from the vessel and/or damage the stent. As an example, as of the filing of this disclosure, SilverHawk™ and TurboHawk™ atherectomy catheters from COVIDIEN are contraindicated for in-stent restenosis at a peripheral vascular site.

SUMMARY

Several embodiments of an operational control mechanism for a tissue-removing catheter that removes tissue from a body lumen are disclosed. In particular, embodiments of the operational control mechanism may be suitable for use with atherectomy catheters for removing (i.e., excising) an atheroma (i.e., plaque) from an arterial wall, including removing plaque due to in-stent restenosis.

Other features will be in part apparent and in part pointed out hereinafter.

BRIEF DESCRIPTION OF THE DRAWINGS

FIG. 4A is an end view of the distal portion of the tissue-removing catheter of FIG. 1 in which the cutter is in an open position outside of the cutting window;

FIG. 4B is a sectional view along line A-A of FIG. 4A;

FIG. 9A is a perspective view of a cutter of the present invention;

FIG. 9B is an end view of the cutter of FIG. 9A;

FIG. 9C is a sectional view of the cutter along line A-A of the cutter of FIGS. 9A and 9B;

FIG. 10A is a perspective view of a cutter of the present invention;

FIG. 10B is an end view of the cutter of FIG. 10A;

FIG. 10C is a sectional view of the cutter along line B-B of the cutter of FIGS. 10A and 10B;

Corresponding reference characters indicate corresponding parts throughout the drawings.

DETAILED DESCRIPTION OF THE DRAWINGS

Figure 1:
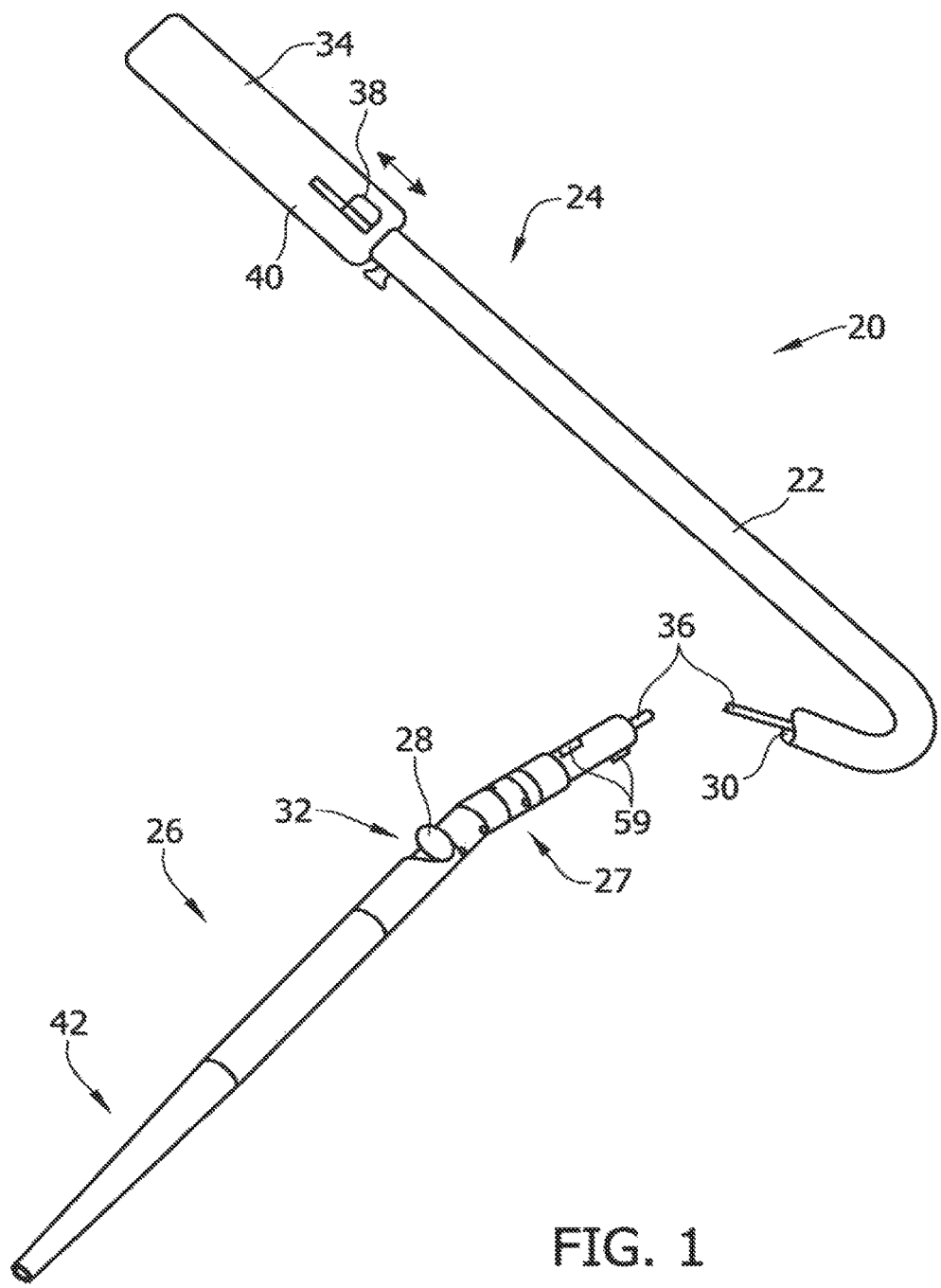
FIG. 1 is a perspective view of one embodiment of a tissue-removing catheter.

Referring now to the drawings, several embodiments of an operational control mechanism for a tissue-removing catheter that removes tissue from a body lumen are disclosed. In particular, embodiments of the operational control mechanism may be suitable for use with atherectomy catheters for removing (i.e., excising) an atheroma (i.e., plaque) from a blood vessel, including removing plaque due to in-stent restenosis and penetrating chronic total occlusions (CTO). The disclosed operational control mechanism embodiments, however, may also suitable for treating stenosis of other body lumens and other hyperplastic and neoplastic conditions in other blood vessels and body lumens, such as the ureter, the biliary duct, respiratory passages, the pancreatic duct, the lymphatic duct, and the like. Neoplastic cell growth will often occur as a result of a tumor surrounding and intruding into a body lumen. While the remaining discussion is directed toward operational control mechanisms for catheters for tissue-removing and passing through atheromatous or thrombotic occlusive material in an artery, it will be appreciated that the operational control systems may be employed with other types of catheters for removing and/or passing through a variety of occlusive, stenotic, or hyperplastic material in a variety of body lumens.

Referring now to FIGS. 1-16, one non-limiting example of a suitable atherectomy catheter, for use with embodiments of the operational control mechanism disclosed below, is generally indicated at 20. It is understood that the operational control mechanism disclosed below may be used with other types of catheters for removing tissue from a body lumen, and is not necessarily limited to "side cutting" atherectomy and tissue-removing catheters.

The illustrated catheter 20 comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A tissue-removing element 28, such as a cutter, as illustrated, is disposed within a lumen 30 of the catheter body 22. The tissue-removing element 28 removes tissue from the lesion or obstruction. It is understood that the tissue-removing element 28 may be another type of element for removing tissue, other than the illustrated cutter, including for example, an abrasive element (e.g., a burr). The cutter 28 is typically rotatable within the distal portion 26 about an axis that is parallel to the longitudinal axis of the distal portion of catheter 20 and axially movable along the longitudinal axis. The cutter 28 can access target tissue through a side opening window 32 in the distal portion 26, which is typically large enough to allow the cutter 28 to protrude through and move out of the window 32 a predetermined distance. The cutter is coupled to a handle, generally indicated at 34 (FIGS. 12-16), through a coiled drive shaft 36. Actuation of an input device or manual actuator 38 on the handle, which forms part of the deployment mechanism in this embodiment, can activate the drive shaft 36 and cutter 28, and move the cutter 28 longitudinally over a cam so as to deflect the distal portion and move the cutter 28 out of cutting window 32. As explained in more detail below, camming of the cutter 28 can cause the distal portion 26 to pivot or deflect relative to the proximal portion 24 so as to deflect and urge the cutter into the tissue in the body lumen.

In some embodiments, the distal portion 26 of the catheter may be moved to an angled or offset configuration from the longitudinal axis of the proximal portion 24 of the catheter and the cutter 28. In some embodiments, the cutter 28 can also be deflected off of the axis of the proximal and/or distal portion of the catheter. Moving the distal portion 26 to an angled/offset position may cause a portion of the catheter 20 to urge against a target tissue, may expose the cutter 28 through the window 32 or both, in various embodiments.

The proximal portion 24 of the catheter body 22 may be relatively flexible and the distal portion 26 may be relatively rigid. Additionally, many embodiments include a flexible distal tip member 42. The flexible proximal portion 24 of the catheter is typically a torque shaft and the distal portion 26 is typically a rigid tubing. The torque shaft, which is indicated by the same reference numeral 24, facilitates transportation of the catheter body 22 and cutter 28 to the diseased site. The proximal end of the torque shaft 24 is coupled to the handle 34 and the distal end of the torque shaft is attached to the distal, rigid portion 26 of the catheter 20 through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body 22 will have the pushability and torqueability such that torquing and pushing of the proximal end will translate motion to the distal portion 26 of the catheter body 22.

Figure 1A:
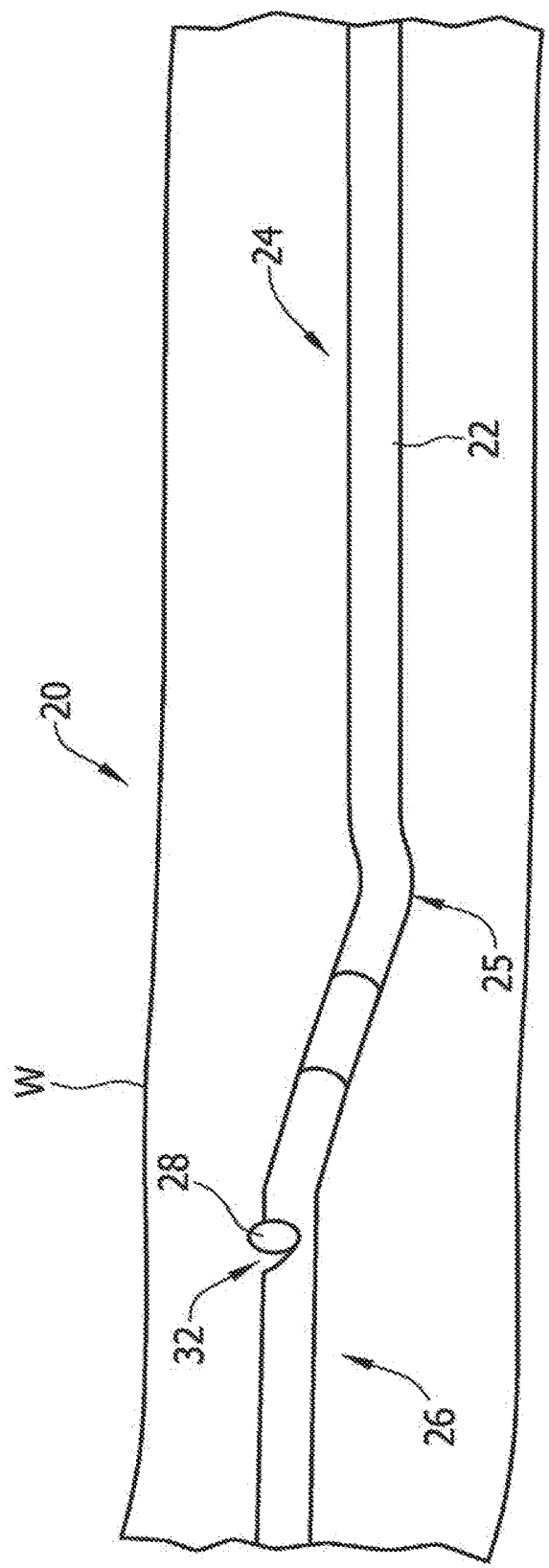
FIG. 1A is a side view of a portion of a tissue-removing catheter as in FIG. 1 in a body lumen, where the body has a distal portion with a bend, according to one embodiment of the present invention.

Referring now to FIG. 1A, the catheter 20 as in FIG. 1 may have a flexible proximal portion 24 which additionally includes urging means 25. As shown in FIG. 1A, urging means 25 may comprise a bent or curved shape towards the distal end of proximal portion 24, which may help urge the cutter 28 or other tissue-removing element toward a wall of a body lumen to enhance treatment. Such a bend increases the working range of the catheter by allowing the cutter to be urged into a lumen wall across a wider diameter.

In other embodiments, urging means 25 may take many other suitable forms. For example, a similar result to the bend may be achieved by including a distal portion that is not permanently bent but that is more rigid on one side than on the opposite side of catheter body 22. Thus, when proximal tension is applied to the proximal portion 24, as when proximal force is applied to the tissue-removing apparatus to expose the cutter 28 through the window 32, the urging means 25 will cause the catheter body 22 to bend toward the less rigid side. The less rigid side will typically be the same side as the window 32, so that the window 32 and/or the cutter 28 will be urged against a wall of a body lumen by the bend. In still other embodiments, a shaped element may be introduced into catheter body 22 to act as urging means 25. Any suitable urging means is contemplated.

Figure 2:
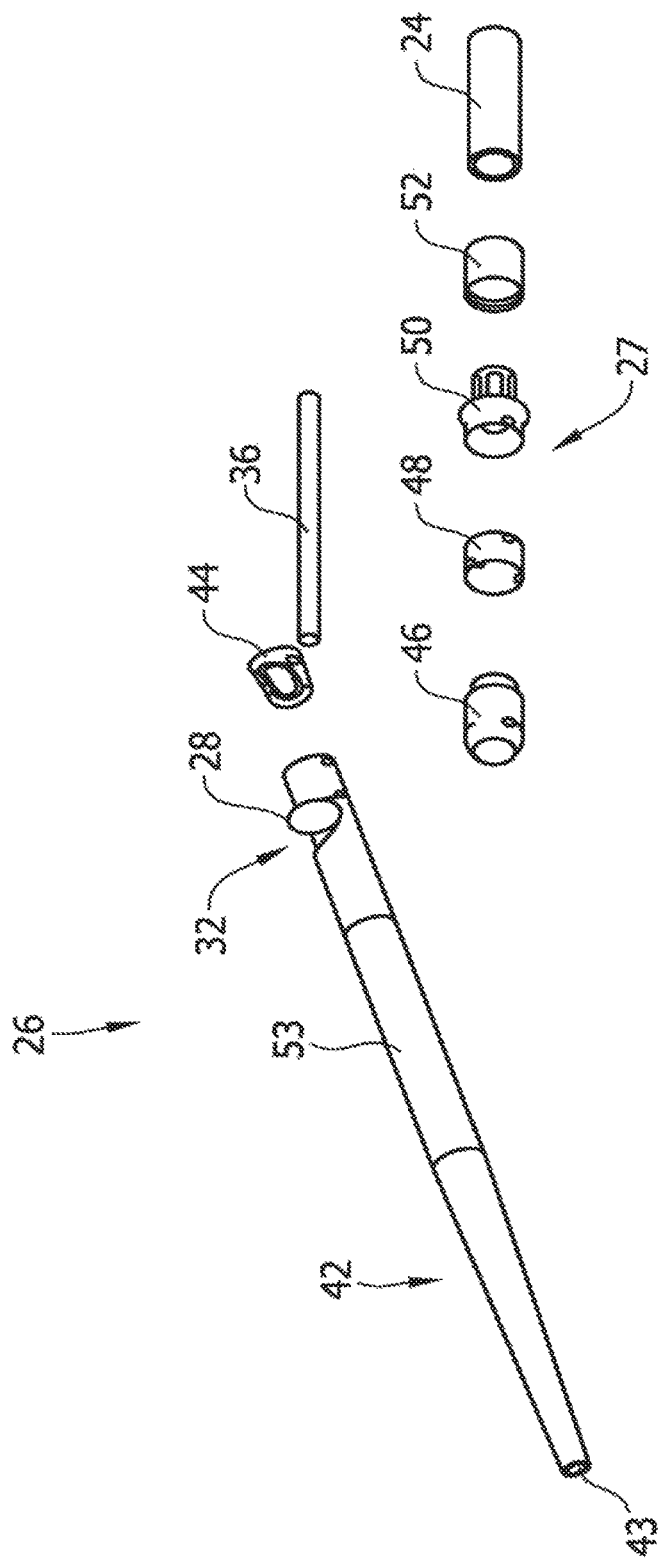
FIG. 2 is an exploded view of an exemplary distal portion of the tissue-removing catheter.

Referring to FIG. 2, the catheter 20 includes the connection assembly 27, the distal portion 26, a distal tip member 42 that at least partially defines a collection chamber 53 for storing the severed atheromatous material, and a lumen that can receive the guidewire. The distal tip member 42 can have a distal opening 43 that is sized to allow an imaging guidewire or conventional guidewire (not shown) to be advanced distally through the tip member. In some embodiments, the distal tip member 42 may also include a distal guidewire lumen (not shown) for allowing passage of a guidewire. For example, some embodiments may include a distal guidewire lumen having a length of between about 1.0 cm and about 5.0 cm, and preferably between about 2.0 cm and about 3.0 cm. Such a distal guidewire lumen may be used alone or in conjunction with a proximal guidewire lumen located on another, more proximal, portion of the catheter 20.

A ramp or cam 44 can at least partially fit within the distal portion 26 of the catheter 20. As will be described in detail below, in many embodiments proximal movement of the cutter 28 over the ramp 44, causes the deflection of the distal housing 26 and guides cutter out of cutting window 32. Attached to the ramp 44 is a housing adaptor 46 that can connect one or more articulation members 48 to the distal tip member 42 to create an axis of rotation of the distal portion 26. The housing adaptor 46 and articulation member 48 allow the distal portion 26 of the catheter 20 to pivot and bias against the body lumen. In the illustrated embodiment there are only one housing adaptor 46 and one articulation member 48, but it should be appreciated that the catheters of the present invention can include, two, three, or more joints (e.g., axis of rotation), if desired. Moreover, the axes of rotation can be parallel or non-parallel with each other.

The catheter 20 can also include a shaft adaptor 50 and collar 52 to couple articulation members 48 to the torque shaft 22. Shaft adaptor 50 can connect the housing to the torque shaft 22 and the collar 52 can be placed over a proximal end of the shaft adaptor and crimped for a secure attachment. It should be appreciated by one of ordinary skill in the art that while one catheter embodiment has the above components that other catheters may include more or fewer of the components described above. For example, some components can be made integral with other components and some components may be left out entirely. Thus, instead of having a separate ramp 44, the ramp may be integrated with the distal portion 26 to direct the cutter 28 out of the cutting window 32.

As shown in FIGS. 3-5, the cutter 28 will generally be movable between two or more positions using a deployment mechanism. In the illustrated embodiment, the actuator 38 actuates operation of the deployment mechanism, although in other embodiment, the deployment mechanism may be actuated by other actuators. In the illustrated embodiment, the deployment mechanism allows for the cutter 28 to be selectively moveable to a stowed or neutral position (FIGS. 3A and 3B) in which the cutter is stowed in the distal portion 26 of the catheter body 22 and is not exposed through the window 32. In some embodiments, an imaging device (not shown) can be coupled to cutter 28 so as to image the body lumen through cutting window 32 when cutter is in the neutral position. Once the catheter 20 has reached the target site, the cutter 28 can be moved proximally to a tissue-removing position (FIGS. 4A and 4B), in which the cutter 28 extends through the cutting window 32 a distance L1 beyond an outer diameter D of the distal portion 26. In some embodiments, in the tissue-removing position, the cutter 28 will have deflected the distal portion 26 and the cutter's axis of rotation will generally be in line with connection assembly 27 but angled or offset from longitudinal axis of the distal portion of the catheter body 22.

Figure 5A:
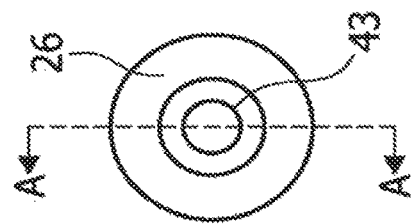
FIG. 5A is an end view of the distal portion of the tissue-removing catheter of FIG. 1 in which the cutter is in a packing position within a tip member of the catheter.
Figure 5B:
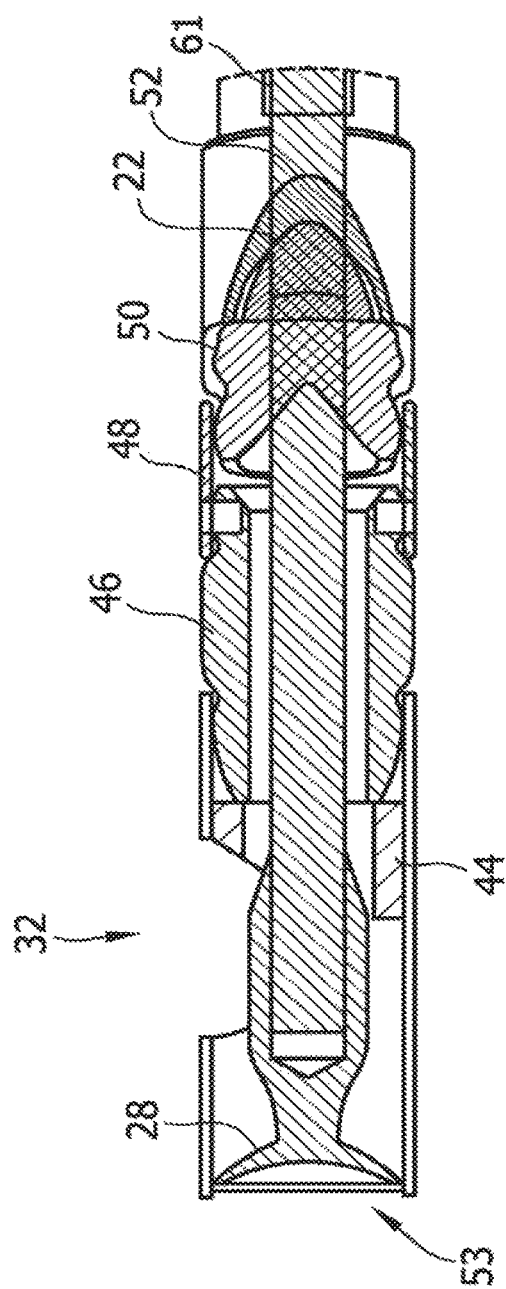
FIG. 5B is a sectional view along line A-A of FIG. 5A.

Optionally, in some embodiments, the cutter 28 can be moved to a packing position, in which the cutter is moved distally, beyond the stowed or neutral position, so as to pack the severed tissue into the distal collection chamber 53 (FIGS. 5A and 5B). It should be appreciated however, that while the exemplary embodiment moves the cutter 28 to the above described positions, in other embodiments the cutter can be positioned in other relative positions. For example, instead of having the neutral position distal of the cutting window, the neutral position may be proximal of the window, and the open position may be along the distal end of the cutting window, or the like.

Referring again to FIGS. 4A and 4B, the interaction of the components of the rigid distal portions 26 in one exemplary embodiment will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter 28 to move out of the cutting window during cutting, but sized and shaped to not expel emboli into the vasculature. The cams or ramp 44 (shown most clearly in FIG. 4B) can be disposed in the distal portion 26 of the catheter body 22 to guide or otherwise pivot the cutter 28 out of the cutting window 32, from the non-exposed, neutral position (FIG. 3B) to the exposed, tissue-removing position (FIG. 4B) as the cutter 28 is pulled proximally through tensioning of drive shaft 36 via the actuator 38. This operation is explained in detail below.

Referring to FIGS. 4A and 4B, a joint 49 is located proximal to the cutting window 32 to provide a pivot point for camming of the distal portion 26 relative to the proximal portion 24. The bending at the joint 49 is caused by the interaction of the cams or ramps 44 with cutter 28 and the tensile force provided through drive shaft 36. In the exemplary configuration, the joint 49 includes a housing adaptor 46 that is pivotally coupled to the distal rigid portion 26. As shown in FIGS. 4A and 4B, the resulting pivoting of the rigid distal portion 26 relative to the proximal portion 24 causes a camming effect which urges the distal portion against the body lumen wall without the use of urging means (e.g., a balloon) that is positioned opposite of the cutting window 32. Thus, the overall cross sectional size of the catheter body 22 can be reduced to allow the catheter 20 to access lesions in smaller body lumens. In exemplary embodiments, the distal portion 26 can deflect off of the axis of the proximal portion 24 of the catheter 20 typically between 0° degrees and 30° degrees, usually between 5° degrees and 20° degrees, and most preferably between 5° degrees and 10° degrees. The angle of deflection relates directly to the urge. Urge, however, does not necessarily relate to force but more to the overall profile of the catheter 20. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

In some embodiments, the deflection of the distal portion 26 of the catheter 20 urges the cutter 28 into the exposed, tissue-removing position (FIG. 4B, such that distal advancement of the entire catheter body 22 can move the rotating cutter through the occlusive material. Because the cutter 28 is moved a distance L1 beyond the outer diameter of the distal portion 26 of the catheter 20 and outside of the cutting window 32, the user does not have to invaginate the tissue into the cutting window. In some embodiments, for example, the cutter 28 can be moved between about 0.025 mm and about 1.016 mm, and preferably between about 0.025 mm and about 0.64 mm, beyond the outer dimension of the distal portion 26. It should be appreciated that the cutter excursion directly relates to the depth of cut. The higher the cutter 28 moves out of the cutting window 32 the deeper the cut. The ranges are chosen around efficacy without risk of perforation of the body lumen.

Figure 3A:
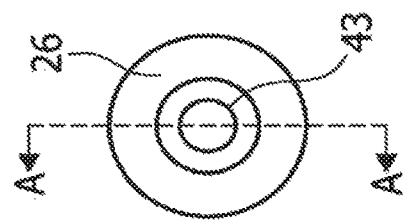
FIG. 3A is an end view of the distal portion of the tissue-removing catheter of FIG. 1 in which the cutter is in a closed position in the catheter body.
Figure 3B:
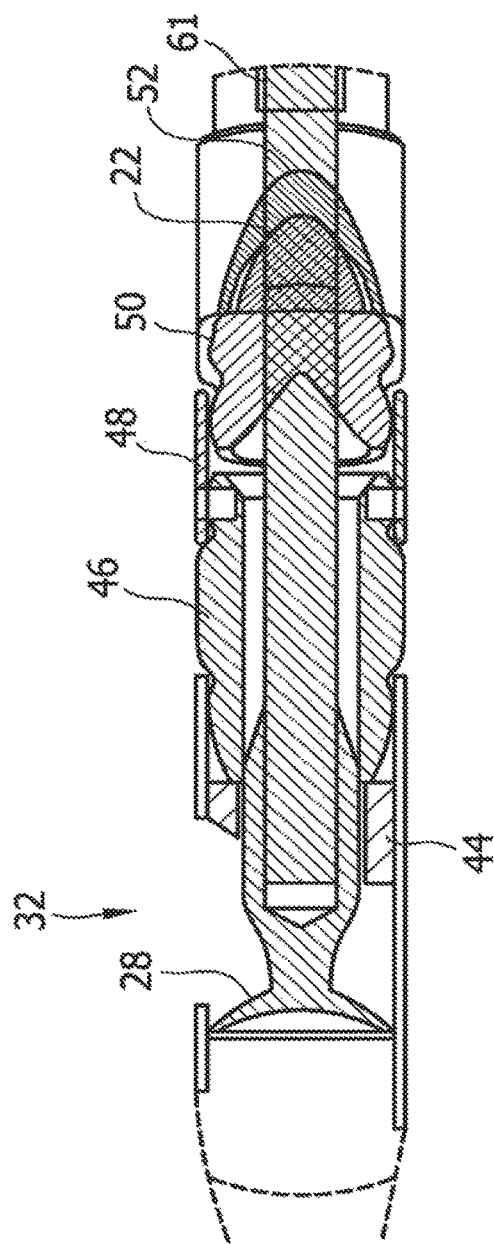
FIG. 3B is a sectional view along line A-A of FIG. 3A.
Figure 3C:
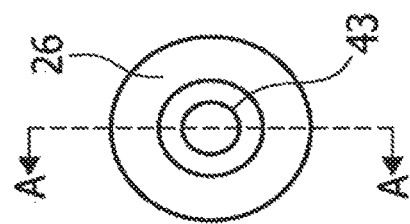
FIGS. 3C and 3D are views of the distal portion of a tissue-removing catheter, where the distal portion has a locking shuttle mechanism.
Figure 3D:
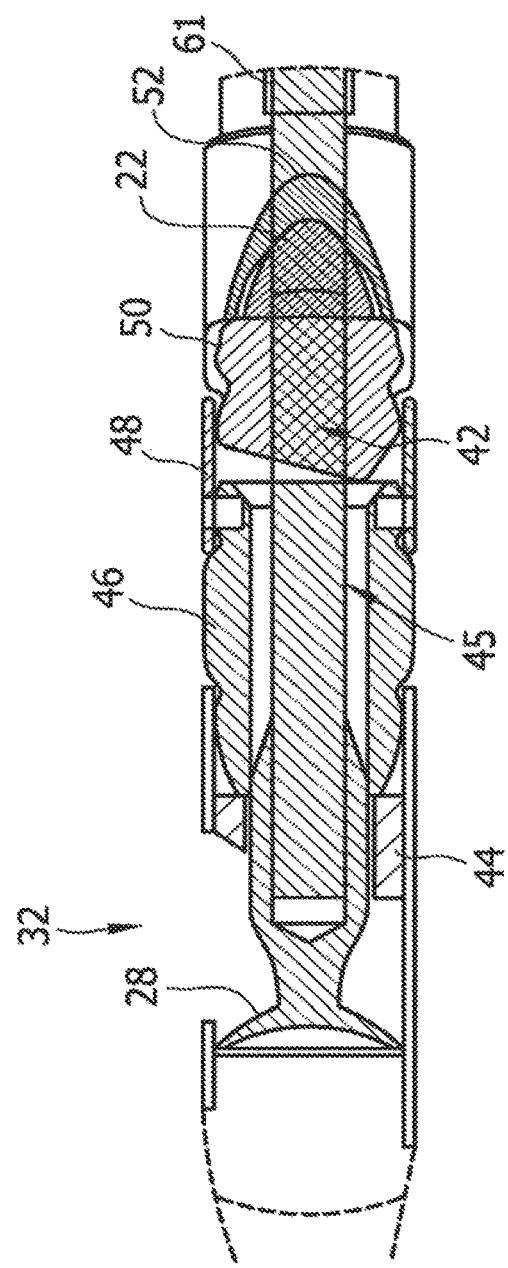
Figure 4C:
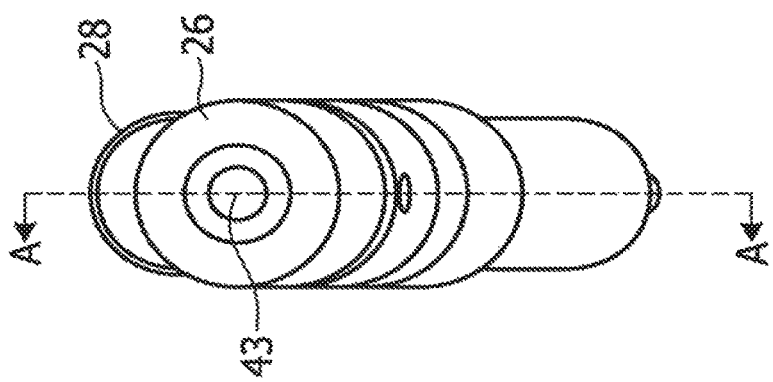
FIGS. 4C and 4D are views of the distal portion of a tissue-removing catheter in which the cutter is in an open position, where the distal portion has a locking shuttle mechanism.
Figure 4D:
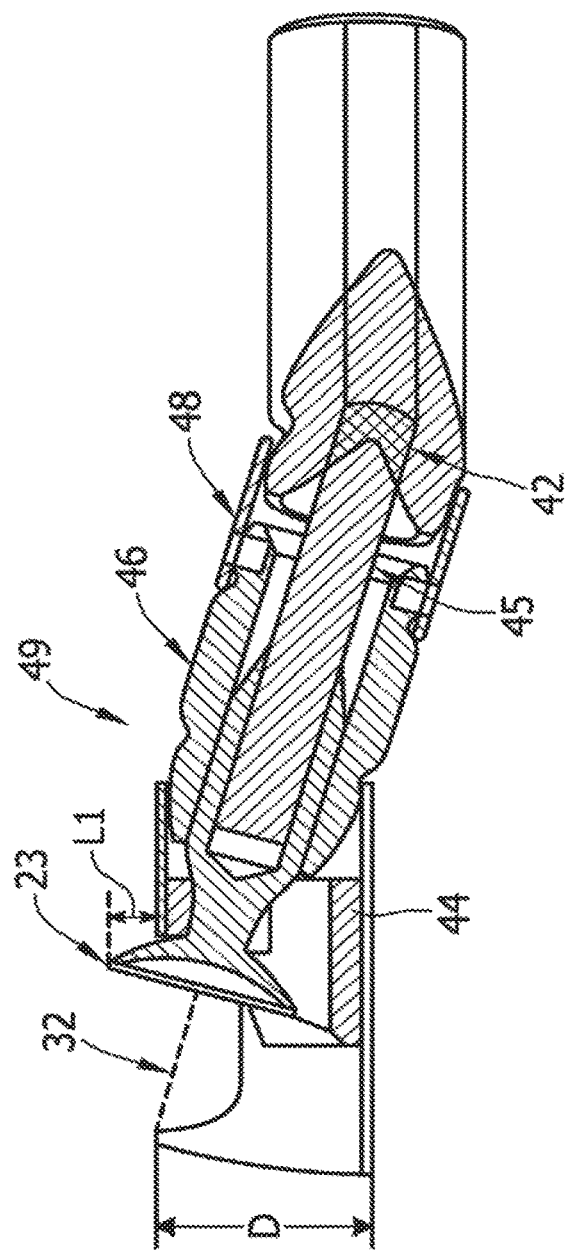

Some embodiments of the catheter 20 include a shuttle mechanism or other similar mechanism for temporarily locking the catheter in the tissue-removing position. FIGS. 3C and 3D illustrate such an embodiment in the neutral, non-tissue-removing position. Such embodiments generally include a shuttle member 45 and a shuttle stop member 42. The shuttle stop member is typically disposed at an angle, relative to a longitudinal axis through the catheter. FIGS. 4C and 4D show the same embodiment in the tissue-removing position. When the cutter 28 is moved into the tissue-removing position in such embodiments, the shuttle member 45 falls into the shuttle stop member 42 and thus locks the cutter 28 in the tissue-removing position. To unlock the cutter 28, the cutter may be advanced forward, distally, to release the shuttle member 45 from the shuttle stop member 42.

Some embodiments including a shuttle mechanism will also include two joints in the catheter body 22. Thus, catheter body 22 will include the distal portion 26, the proximal portion 24 and a middle portion. When shuttle mechanism is activated to expose cutter 28 through window 32, the middle portion may orient itself at an angle, relative to the proximal and distal portions, thus allowing cutter to be urged towards a side of a lumen. Such a two-jointed configuration may provide enhanced performance of the catheter 20 by providing enhanced contact of the cutter 28 with material to be debulked form a body lumen.

Pushing the entire catheter 20 across a lesion removes all or a portion of the lesion from the body lumen. Severed tissue from the lesion is collected by directing the removed tissue into the collection chamber 53 in the tip member 42 via the cutter 28. Once the catheter 20 and cutter 28 have moved through the lesion, the cutter can be advanced distally to "part off position" the lesion. During "parting off", the cutter 28 is moved distally from the tissue-removing position back into the cutting window 32 (FIG. 3B) and to its neutral or stowed position. The collection chamber 53 of the tip member 42 acts as a receptacle for the severed material, to prevent the severed occlusive material from entering the body lumen and possibly causing downstream occlusions. After "parting off", the cutter 28 can be moved distally to a packing position, in which the cutter moves distally within the collection chamber 53 to pack the severed tissue into collection chamber 53 (FIG. 3B). Typically, the collection chamber 53 will be large enough to allow multiple cuts to be collected before the catheter 20 has to be removed from the body lumen. When the collection chamber 53 is full, or at the user's discretion, the catheter 20 can be removed, emptied and reinserted over the guidewire.

In various embodiments, enhancements to the collection chamber 53 may be included. For example, in some embodiments the collection chamber 53 may be configured to be partially or completely translucent or radiolucent and a portion of the catheter 20 surrounding or adjacent to the window 32 will be radiopaque. This combination of radiolucent collection chamber 53 and radiopaque material adjacent window 32 will enhance the ability of a user to determine how full the collection chamber 53 is, because the fullness of the collection chamber will be directly related to the distance the cutter 28 can advance forward into the collection chamber 53. By facilitating the assessment of collection chamber filling, these embodiments will reduce the need for manually withdrawing the catheter to examine the collection chamber 53.

Figure 6:
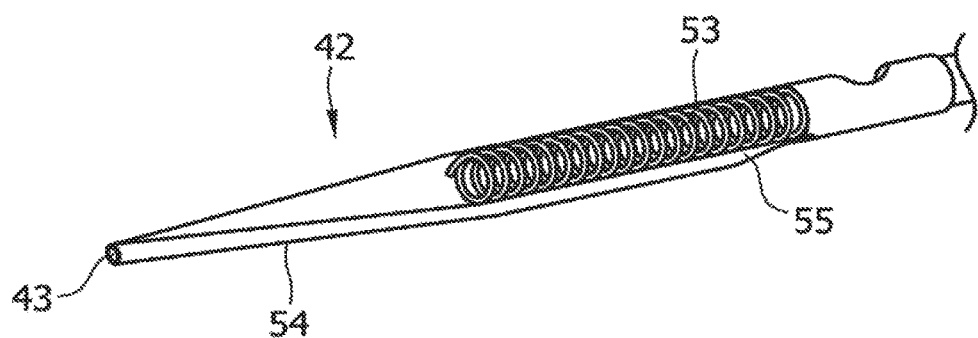
FIGS. 6 to 8 illustrate a monorail delivery system of the present invention.
Figure 7:
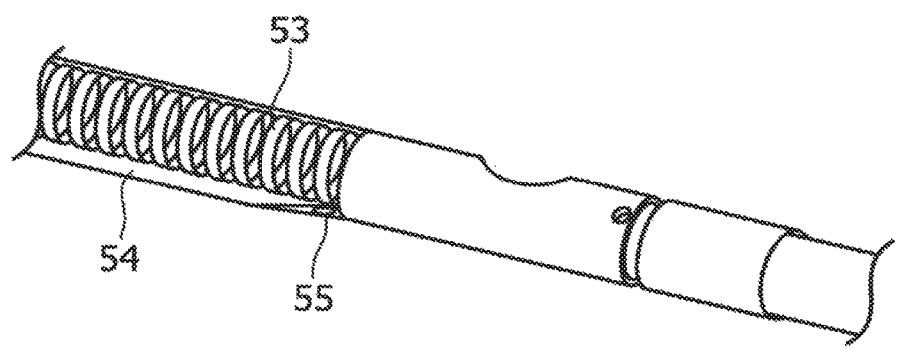
Figure 8:
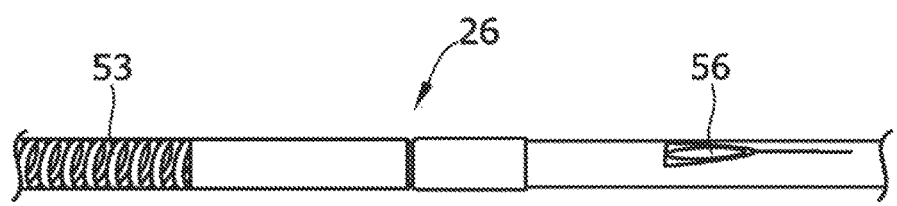

FIGS. 6 through 8 illustrate one exemplary monorail delivery system to assist in positioning the cutter 28 at the target site. For example, tip member 42 of the catheter can include a lumen 54 having a distal opening 43 and a proximal opening 55 that is sized to receive a guidewire, having a diameter of about 0.014 in., about 0.018 in., about 0.032 in. or any other suitable diameter.

The catheters 20 can include radiopaque markers so as to allow the user to track the position of the catheter under fluoroscopy. For example, as already described, a point or area around or adjacent to the window 32 may be made radiopaque. In other embodiments, the distal portion 26 can be radiopaque and radiopaque markers can be disposed on the flexible shaft 36. Typically, the markers will be disposed along the top, proximal to the cutting window 32, and on the bottom of the catheter 20 to let the user know the position of the cutter and cutting window relative to the target site. If desired, the top and bottom markers can be different shaped so as to inform the user of the relative orientation of the catheter 20 in the body lumen. Because the guidewire will form a helix in its transition from lumen 56 to tip member lumen 54, the user will be able to view the top and bottom radiopaque markers without interference from the guidewire. Some embodiments of the catheter 20 can also include a radiopaque cutter stop 61 (FIG. 3B) that is crimped to driveshaft 36 proximal of the cutter that moves with the cutter so as to let the user know when the cutter 28 is in the open position.

FIGS. 9A through 11D show some exemplary embodiments of the cutter 28. The distal portion 60 of the rotatable cutter 28 can include a serrated knife edge 62 or a smooth knife edge 64 and a curved or scooped distal surface 66. The distal portion 60 may have any suitable diameter or height. In some embodiments, for example, the diameter across the distal portion 60 may be between about 0.1 cm and about 0.2 cm. A proximal portion 68 of the cutter 28 can include a channel 70 that can be coupled to the drive shaft 36 that rotates the cutter. As shown in FIGS. 10A-10C, some embodiments of the cutters 28 can include a bulge or bump 69 that is provided to interact with a stent so as to reduce the interaction of the cutting edge with the stent. In any of the foregoing embodiments, it may be advantageous to construct a serrated knife edge 62, a smooth knife edge 64, or a scooped distal surface 66 out of tungsten carbide.

Figure 11A:
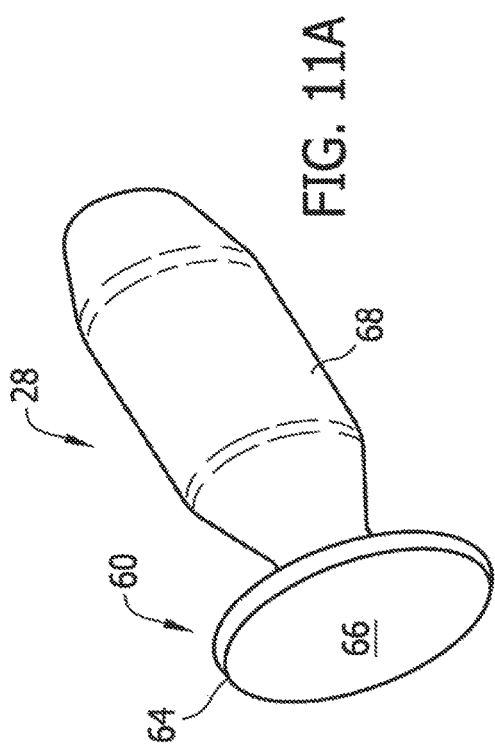
FIG. 11A is a perspective view of another cutter of the present invention.
Figure 11C:
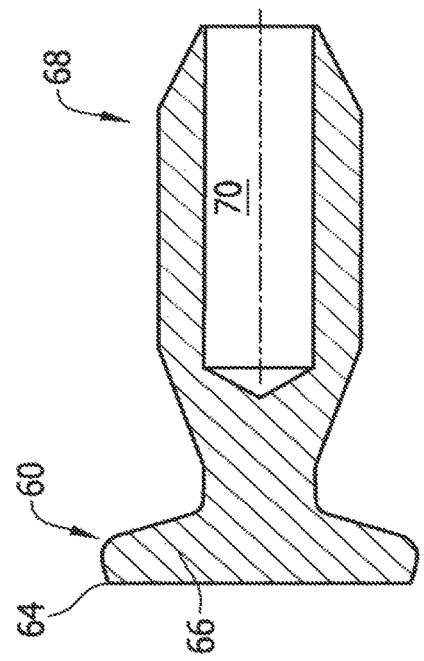
FIG. 11C is a sectional view of the cutter along line C-C of the cutter of FIGS. 11A and 11B.
Figure 11B:
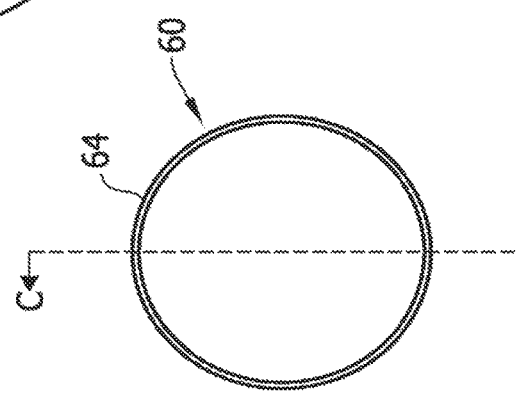
FIG. 11B is an end view of the cutter of FIG. 11A.
Figure 11D:
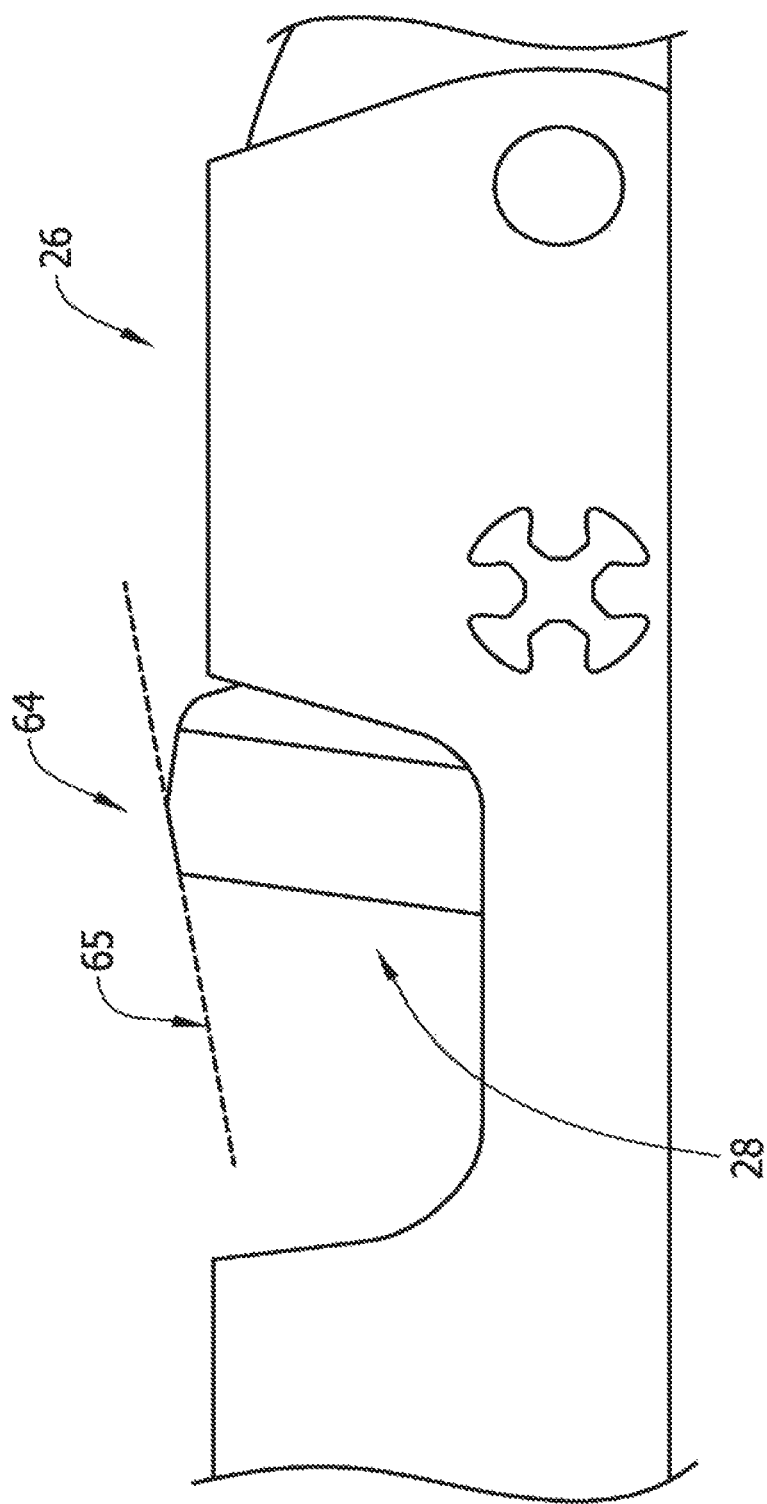
FIG. 11D is a side view of another embodiment of a cutter, shown partially within a catheter body.

Another embodiment of a cutter 28 shown in side view within a distal portion 26 in FIG. 11D. In this embodiment, the cutter 28 has a beveled edge 64, made of tungsten carbide, stainless steel, titanium or any other suitable material. The beveled edge 64 is angled inward, toward the axis of rotation (or center) of the cutter 28, creating a "negative angle of attack" 65 for the cutter 28. Such a negative angle of attack may be advantageous in many settings, when one or more layers of material are desired to be debulked from a body lumen without damaging underlying layers of tissue. Occlusive material to be removed from a vessel typically has low compliance and the media of the vessel (ideally to be preserved) has higher compliance. A cutter 28 having a negative angle of attack may be employed to efficiently cut through material of low compliance, while not cutting through media of high compliance, by allowing the high-compliance to stretch over the beveled surface of cutter.

Referring to FIGS. 12 through 16, one embodiment of the handle 34 will now be described in detail. The handle 34 includes a housing 40 that is sized and shaped to be held in a hand of the user. An electric motor 74 (e.g., a DC motor) is contained in the housing 40, along with a power source 76 (e.g., a battery or other source of DC power) electrically connected to the motor for powering the motor. The drive shaft 36 is operatively coupled to the motor 74 when the catheter 20 is connected to the handle 34 for driving rotation of the drive shaft and the cutter 28. In some embodiments, at maximum power the motor 74 can rotate drive shaft 36 between 1,000 rpm and 10,000 rpm or more, if desired. The manual actuator 38 (e.g., a lever, as illustrated) on the exterior of the housing 40 allows the user to control operations of the catheter 20. For example, in the illustrated embodiment the lever 38 is axially moveable relative to the housing 40. In particular, the lever 38 is movable to a neutral position (shown in FIG. 14), whereby the cutter 28 is in its non-exposed, neutral position (FIG. 3D). To expose the cutter 28 and activate the motor 74 to drive rotation of the cutter, the lever 38 is moved proximally from the neutral position to a proximal, tissue-removing position of the lever (see FIG. 15) to move the cutter proximally and out of cutting window 32 (FIG. 4B) to its tissue-removing position and simultaneously activate the motor 74. For example, proximal movement of the lever 38 to the proximal position may actuate (e.g., depress) an electrical switch 78 that electrically connects the power source 76 to the motor 74. To part off tissue, the lever 38 is moved distally from the proximal, tissue-removing position, back to its neutral position (FIG. 14) to drive (i.e., move) the cutter 28 distally into the distal portion of the catheter 20 (FIG. 3D). As the lever 38 is positioned in its neutral position, the electrical switch 78 is released (i.e., opened) so as to deactivate the electric motor 74. To pack the removed tissue in the collection chamber 53 of the distal tip member 42, the lever 38 is moved distally from the neutral position to a distal position, packing position of the lever (see FIG. 16) to drive (i.e., move) the cutter 28 distally into the collection chamber and to its packing position (FIG. 5B). It should be appreciated, while the figures illustrate the use of an lever 38 or thumb switch, other embodiments of the present invention can use other types of actuators, such as separate buttons (e.g., a close window button, debulk tissue button, and packing button), or the like.

Figure 17:
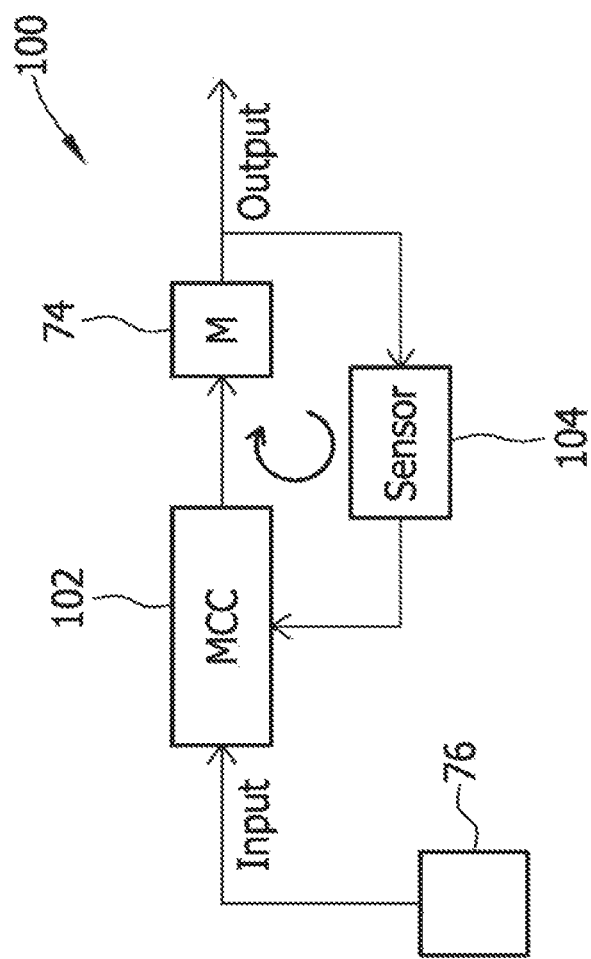
FIG. 17 is an exemplary block diagram of the first embodiment of the operational control mechanism.

As set forth above, the catheter 20 includes one or more operational control mechanisms for automatically controlling one or more operations of the catheter. Referring to FIGS. 12-19, in a first embodiment, the operational control mechanism comprises a motor control mechanism 100 (FIGS. 13, 17, and 18), which functions to automatically reduce the electric power (e.g., current) supplied to the cutter motor 74 from the power source 76 if the motor control mechanism detects that the cutter 28 is engaging a material having a hardness that is greater than a predetermined threshold hardness. For example, the motor control mechanism 100 may detect that the cutter 28 is engaging a stent or other non-tissue implant, for example, or that the cutter is engaging hardened tissue (e.g., calcified plaque). The motor control mechanism 100 may be housed in the handle 34, as in the illustrated embodiment, or located elsewhere on the catheter 20. A block diagram of this motor control mechanism, including the motor 74, is illustrated in FIG. 17. As shown in FIG. 17, the motor control mechanism 100 includes a motor control circuit 102 connected between the power source 76 and the motor 74. The motor control circuit 102 regulates the amount of power (i.e., current) that is supplied to the motor 74 for operating the motor and driving rotation of the cutter 28.

Referring still to FIG. 17, in an embodiment, the motor control mechanism 100 also includes a sensor 104 that senses an operating parameter of the motor 74, such as a parameter that is indicative of the amount of electrical power being drawn by the motor 74 at some instantaneous time during the cutting operation of the catheter 20. The sensor 104 sends a signal to the motor control circuit 102 that is indicative of the detected operating parameter (e.g., a signal indicative of the amount of power being consumed by the motor 74). The motor control circuit 102 regulates the amount of power supplied to the motor 74 based on the signal it receives from the sensor 104. Thus, the motor control mechanism 100 comprises a feedback loop, as shown in FIG. 17.

Figure 18:
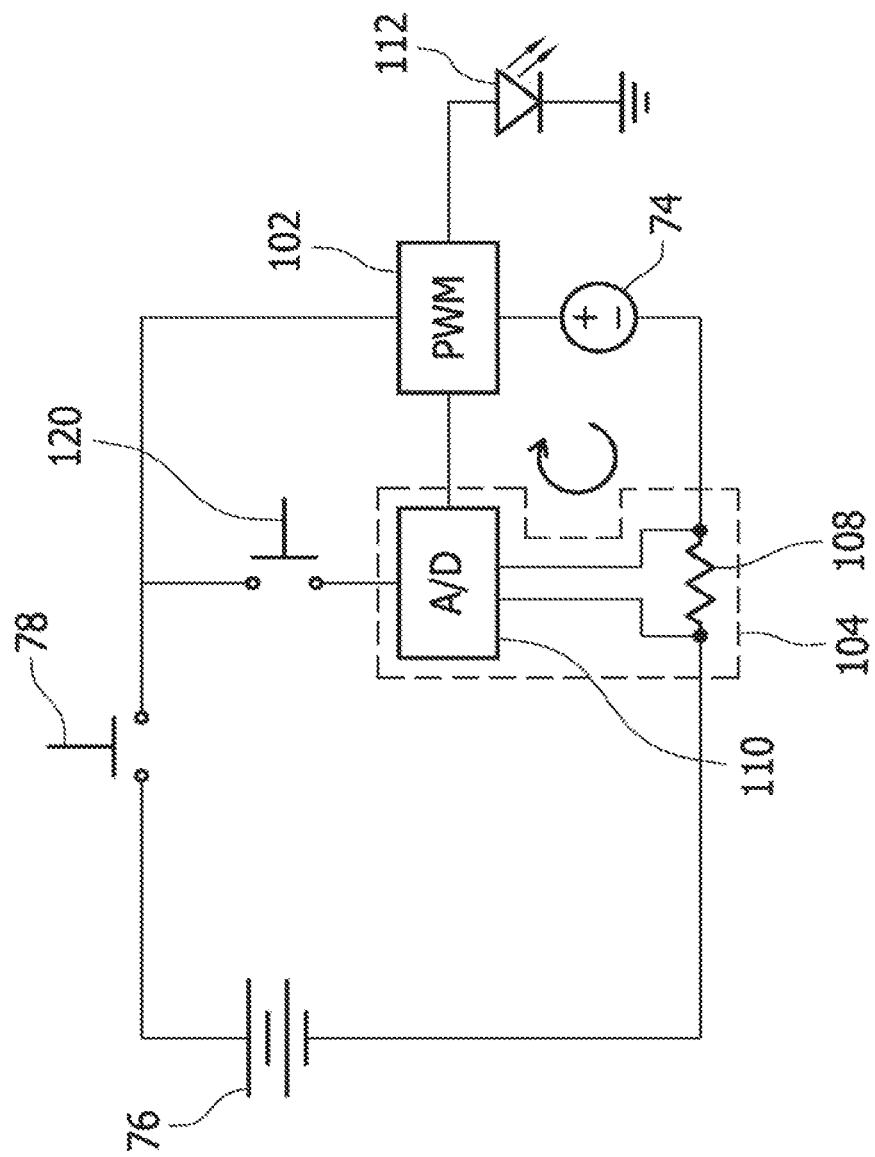
FIG. 18 is an exemplary schematic of the first embodiment of the operational control mechanism.

In one non-limiting example illustrated in FIG. 18, the motor control circuit 102 comprises a pulse width modulation (PWM) circuit (indicated by the same reference numeral 102). The PWM circuit 102 may comprise a microcontroller that is programmed to regulate the amount of power supplied to the motor 74 by outputting a duty cycle signal to the motor based on the signal received from the sensor 104. It is understood that the motor control circuit 102 may comprise other types of devices, other than a microcontroller, and the PWM circuit may operate suitably without the use of a microcontroller. In the same illustrated example (or another example), the sensor 104 comprises a current sensing resistor 108 and an analog-to-digital (A/D) converter 110 in communication with the current sensing resistor. The A/D converter 110 detects the voltage drop across the current sensing resistor 108, which is indicative of the amount of power being drawn by the motor 74 at some instantaneous time. The analog input is converted to a digital signal by the A/D converter 110. This digital signal is inputted to the PWM circuit 102 (or other motor control circuit). The PWM circuit 102 outputs a duty cycle to the motor 74 based, at least in part, on this digital signal. It is understood that sensor 104 may be of other types and configurations without departing from the scope of the present invention. For example, the sensor may be configured to detect the speed and/or the torque of the motor. Other sensors that detect a parameter of the motor that is indicative of the power consumed by the motor are within the scope of the present invention. It is also understood that a motor control circuit configured to detect a parameter of the motor and regulate power supplied to the motor, may be of other configurations, other than illustrated and described above, without departing from the scope of the present invention.

In one non-limiting example, the motor control circuit 102 may be configured to shut off the motor 74, or significantly reduce the power (i.e., current) supplied to the motor a predetermined amount, to thereby reduce the speed of the motor if the motor control circuit determines that the motor is drawing power (e.g., current) that is at or above a predetermined threshold power level (e.g., threshold amperage). For example, the motor control circuit 102 may reduce the speed of the motor 74 to from 0 rpm to about 1000 rpm upon making such a determination. In such an example, the predetermined threshold power level is indicative of the cutter 28 engaging a material having a hardness that is greater than a predetermined threshold hardness (e.g., a stent or other non-tissue implant, or hardened tissue, such as calcified plaque). The motor control circuit 102 shuts off or significantly reduces the speed of the motor 74 to inhibit the catheter 20 from becoming entangled with the stent. In one non-limiting example, where the motor control circuit 102 includes a PWM circuit, the PWM circuit may output a duty cycle from about 0% to about 10% to shut off or significantly reduce the speed of the motor 74.

Figure 12:
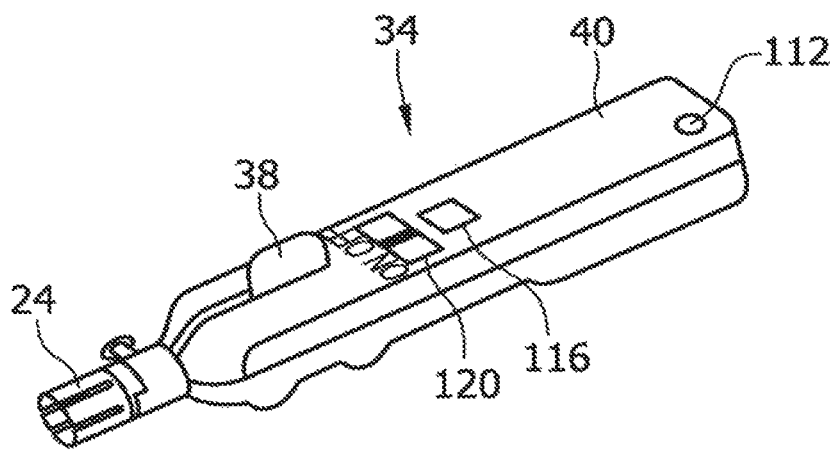
FIG. 12 is a perspective of a first embodiment of a handle for the tissue-removing catheter, including a first embodiment of an operational control mechanism.
Figure 13:
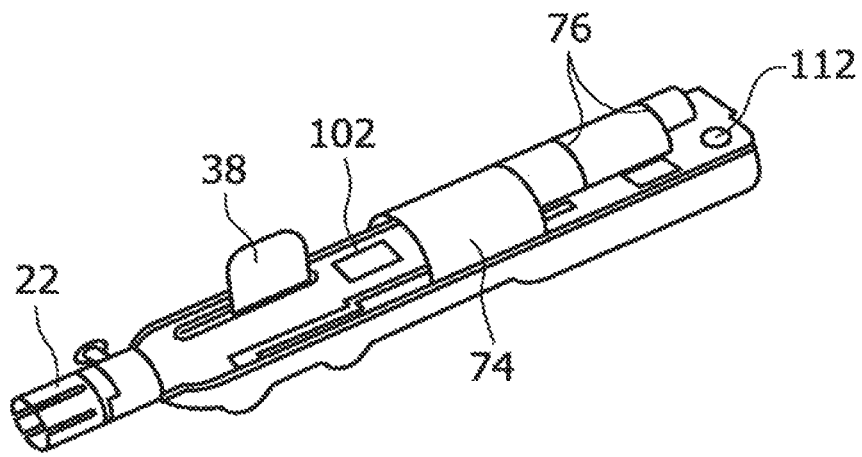
FIG. 13 is similar to FIG. 12 with a cover of the handle removed.
Figure 14:
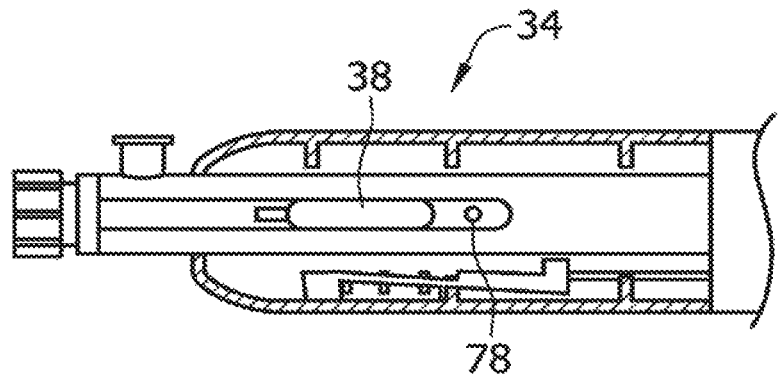
FIG. 14 illustrates a neutral position of a lever of the handle.
Figure 15:
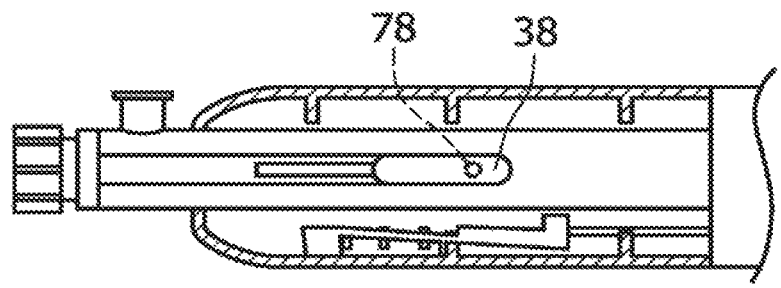
FIG. 15 illustrates a tissue-removing position of the lever of the handle.
Figure 16:
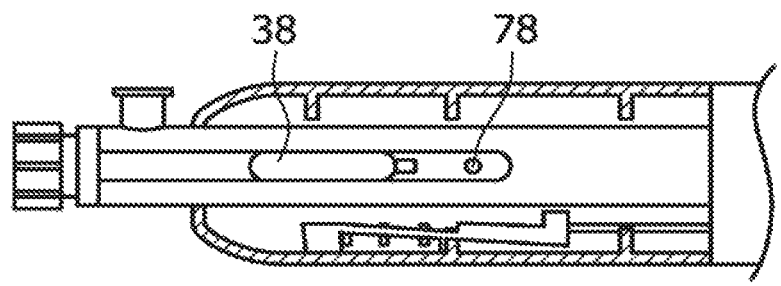
FIG. 16 illustrates a packing position of the lever of the handle.

Referring to FIGS. 18, 12, and 13, the motor control mechanism 100 may include an indicator 112 (e.g., an LED) for communicating to the user that the motor control circuit 102 determined that the cutter 28 has engaged an obstruction and the motor control circuit is shutting off (or has already shut off), or is reducing the power supplied to, the motor 74. In one example, shown in FIG. 18, the indicator 112 (e.g., LED) is activated by the motor control circuit 102. In such an embodiment, the motor control circuit 102 may be a micro-controller. In another example, the indicator 112 may be a device that provides tactile or audible feedback to the user. Other types of indicators for communicating to the user that the motor control circuit 102 is shutting off the motor 74 (or has already shut off) or is significantly reducing the power supplied to the motor do not depart from the scope of the present invention.

The motor control mechanism 100 may include a reset input mechanism 116 (FIG. 12) for resetting the motor control mechanism after the motor control circuit 102 shuts off, or significantly reduces the speed of, the motor 74. The reset input mechanism 116 may comprise a manual switch or button (as shown in FIG. 12) on the handle 34 or may comprise an automatic reset component within the motor control mechanism 100. It is envisioned that after the motor control circuit 102 shuts off, or significantly reduces the speed of, the motor 74, the user will take necessary steps to assess the circumstances surrounding the motor control circuit detecting an obstruction and/or prevent further the cutter 28 from further engaging the obstruction. For example, where the catheter 20 includes an IVUS, the user may view an image of the target site to confirm that the catheter is engaging a stent or other non-tissue obstruction, or otherwise assess the situation. After making the assessment, the user may reset the motor control mechanism 100, and resume treatment.

In one non-limiting example, the catheter 20 may be configured to allow a user to selectively activate and deactivate the above-described operational control function of the motor control mechanism 100. For example, if a stent or other implanted structure is not present in the target body lumen (or at least it is believed that a stent is not present or will not be interfered with), the user can deactivate the operational control function of the motor control mechanism 100 to prevent the motor 74 from shutting off or reducing in speed if the cutter 28 engages hardened tissue (e.g., calcified plaque). It is envisioned that in some cases, the motor 74 may draw power that is at or above the threshold power level when the cutter 28 engages hardened tissue. Thus, if the operational control function of the motor control mechanism 100 is activated, the motor control circuit 102 may shut off or significantly reduce the speed of the motor 74 when the cutter 28 engages hardened tissue, and in some circumstances, this is undesirable. In one example (FIG. 12), the handle 34 may include a switch 120 (or other input mechanism) for selectively deactivating or activating the motor control circuit 100.

Figure 19:
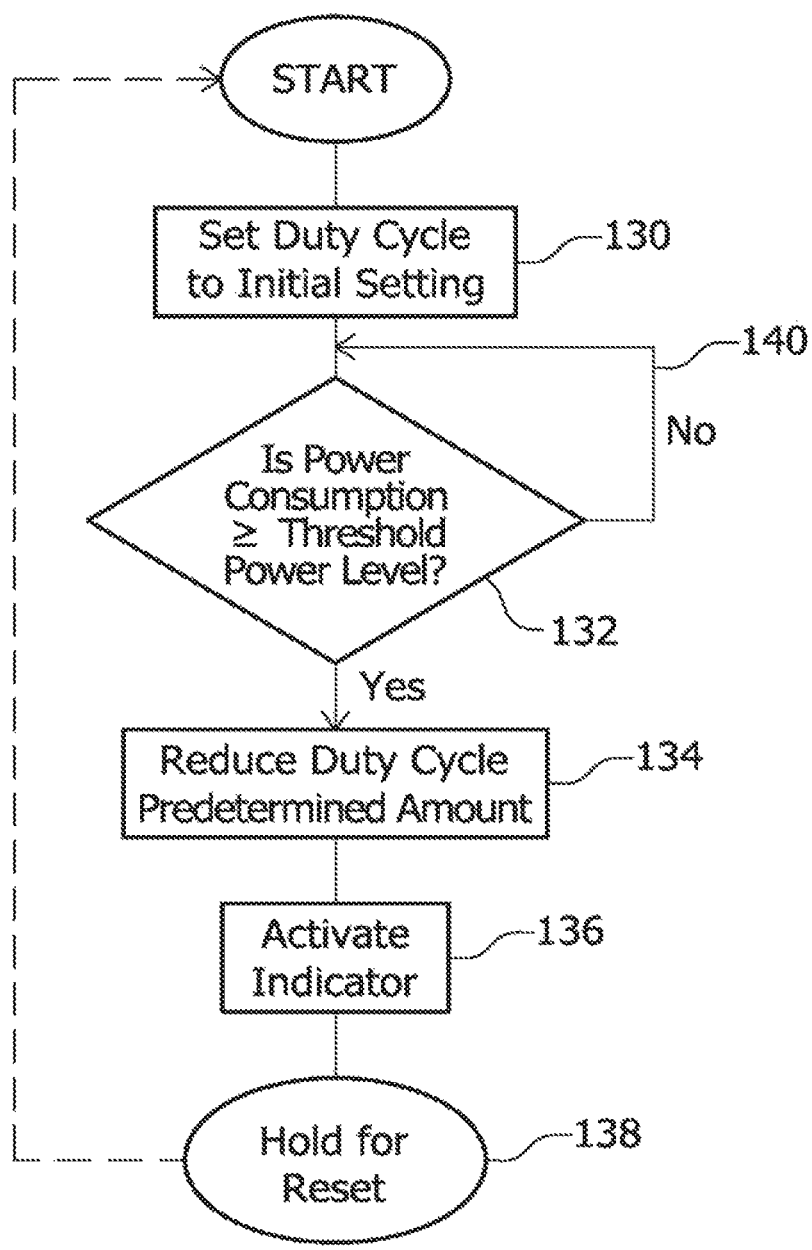
FIG. 19 is an exemplary flow diagram for a motor control circuit of the first embodiment of the operational control mechanism.

An exemplary flow diagram for the motor control circuit 102 of the present embodiment is shown in FIG. 19. In this example, the motor control circuit 102 includes the PWM circuit, which includes a microcontroller for regulating the duty cycle supplied to the motor 74. When the motor control mechanism 100 is active (e.g., such as by activating the motor control mechanism using the switch 120), the microcontroller sets the duty cycle to an initial duty cycle at step 130. At step 132, the microcontroller determines, based on the signal from the sensor 104 and during the cutting operation of the catheter 20, whether the electrical power drawn by the electric motor 74 is at least one of equal to and greater than a predetermined threshold power level. The predetermined threshold power lever is indicative of the cutter 28 engaging, a material having a hardness that is greater than a predetermined threshold hardness (e.g., a stent or other non-tissue implant, or hardened tissue, such as calcified plaque). If the microcontroller determines that the electrical power being drawn by the electric motor 74 is at least one of equal to and greater than a predetermined threshold power level, then at step 134 the microcontroller reduces the amount of power supplied to the motor 74 (i.e., reduces the duty cycle) to shut off, or significantly reduce the speed of, the motor. At step 136, the microcontroller activates the indicator 112 to communicate to the user that the cutter is engaging a hard material, and that the motor 74 is being (or has been) shut down or reduced in speed. This shut down or reduced speed mode of the motor 74 is continued until (or unless) a reset is activated, such as by a user activating the reset button 116, at step 138. If the microcontroller determines that the electrical power being drawn by the electric motor 74 is not at least one of equal to and greater than a predetermined threshold power level, then detection of electrical power consumption by the motor is continued at step 140, which may include a delay. It is understood that the steps involved in determining that the cutter 28 is engaging an obstruction and subsequently reducing the speed of the motor 74 may be other than described above. Moreover, these steps may be performed using analog and/or digital circuits, without the use of a microcontroller.

Referring to FIGS. 20-27, in a second embodiment, an operational control mechanism comprises a locking control mechanism 150 which functions to inhibit the user from moving the cutter 28 from the tissue-removing position (FIG. 4B) back to the neutral position (FIG. 3D) if the locking control mechanism detects that the cutter 28 is engaging a stent or other non-tissue implant, for example. An exemplary handle in which the locking control mechanism 150 may be housed is indicated generally at 34' in FIGS. 23-27. It is understood that the locking control mechanism 150 may be in other locations of the catheter 20. The following components of the handle 34' may be similar or identical to the corresponding components of the first handle 34: a housing 40'; a lever 38' (broadly, an actuator); a motor 74'; and a power source 76'. Other components of the present handle 34', including the locking control mechanism 150, are described herein below. Moreover, the present handle 34' may be used with the same catheter 20 described above herein, and therefore, components of the catheter will be indicated by the same reference numbers set forth above.

Figure 20:
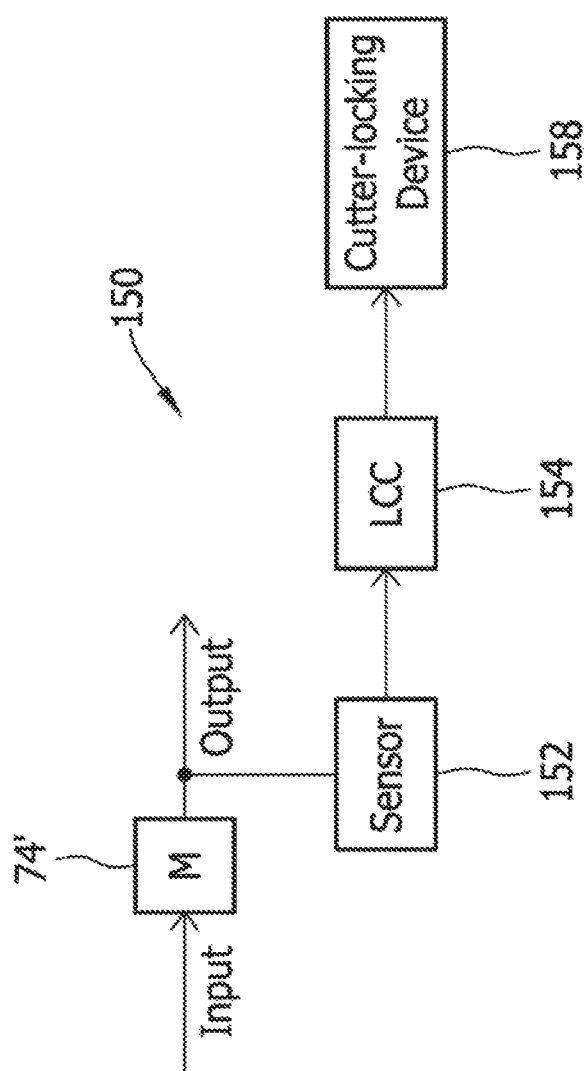
FIG. 20 is an exemplary block diagram of a second embodiment of the operational control mechanism.

A block diagram of one example of the locking control mechanism 150, including the motor 74', is illustrated in FIG. 20. The locking control mechanism 150 includes a sensor 152, which may be identical or similar to the sensor 104 in the motor control circuit 100, and a locking control circuit 154 in communication with the sensor. The locking control circuit 154 receives a signal from the sensor 152 that is indicative of the power being drawn by the motor 74' and determines whether the power being drawn by the motor 74' is at or above a predetermined threshold power level. The locking control circuit 154 is in communication with and actuates a locking device 158. The locking device 158 is selectively configurable between a locked configuration (FIG. 26), in which the locking device inhibits movement of the cutter 28 from its tissue-removing position to its neutral position, and an unlocked configuration (FIGS. 25 and 27), in which the locking device allows movement of the cutter from its tissue-removing position to its neutral position. During normal operation, the locking device 158 is in its unlocked configuration. If the power being drawn by the motor 74' is at or above the predetermined threshold power level, then the locking control circuit 154 configures the locking device 158 to its locked configuration to inhibit movement of the cutter 28 from its tissue-removing position to its neutral position. By restricting movement of the cutter 28 from its tissue-removing position to its neutral position after determining that the cutter is engaging a non-tissue obstruction (e.g., a stent), the locking control circuit 154 inhibits the user from pushing the non-tissue obstruction into the distal portion 26 of the catheter body 22, which may further lead to the non-tissue obstruction becoming entangled with the drive shaft 36 of the catheter 20.

Figure 21:
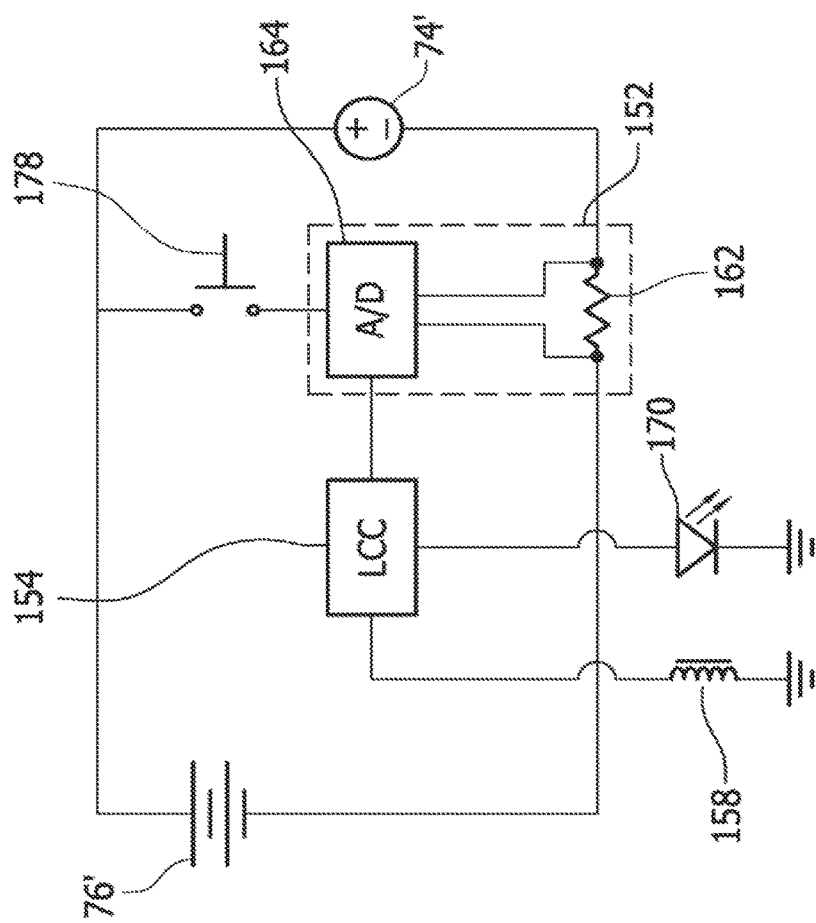
FIG. 21 is an exemplary schematic of the second embodiment of the operational control mechanism.

In one non-limiting example illustrated in FIG. 21, the sensor 152 of the locking control mechanism 150 includes a current sensing resistor 162 and an analog-to-digital (A/D) converter 164 in communication with the current sensing resistor. Like the first embodiment illustrated in FIG. 18, the present A/D converter 164 detects the voltage drop across the current sensing resistor 162, which is indicative of the amount of power being drawn by the motor 74' at some instantaneous time. The analog input is converted to a digital signal by the A/D converter 164. This digital signal is inputted to the locking control circuit 154 (e.g., a microcontroller). If the locking control circuit 154 determines that the power being drawn by the motor 74' is at or above the predetermined threshold power level, then the locking control circuit 154 may actuate the cutter-locking device 158 to configure the locking device in its locked configuration. In this example, the locking device 158 comprises an electromechanical solenoid (or other device). When the solenoid 158 is configured in its locked configuration, it inhibits movements of the lever 38 from its tissue-removing position to its neutral position. As shown in FIGS. 24-27, the locking solenoid 158 is positioned adjacent the lever 38, such that when activated by the microcontroller 154, an armature 158a of the electromechanical solenoid blocks the path of the lever to inhibit the lever from moving to its neutral position. It is understood that the locking control mechanism 150, which is configured to detect an operating parameter of the motor 74' and restrict movement of the cutter 28, may be of other configurations, other than illustrated and described above, without departing from the scope of the present invention.

Figure 24:
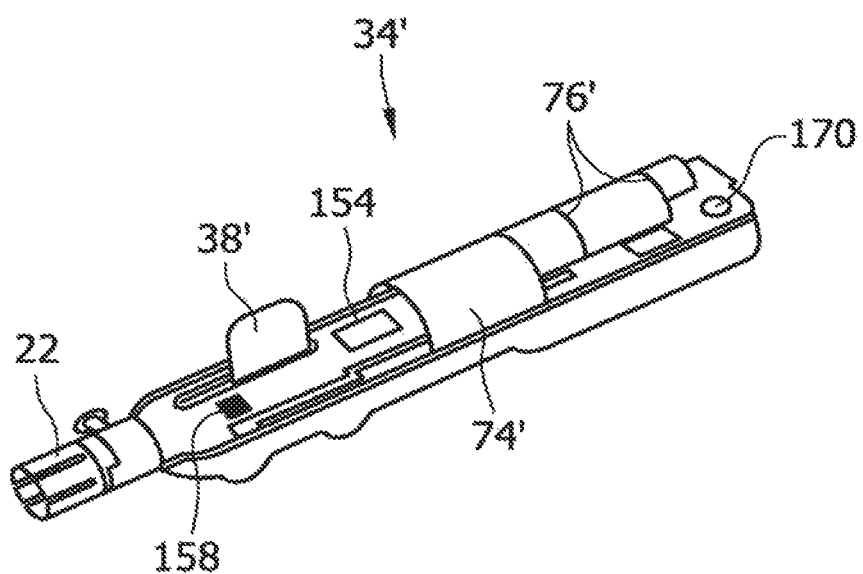
FIG. 24 is similar to FIG. 23, with a cover of the handle removed.
Figure 25:
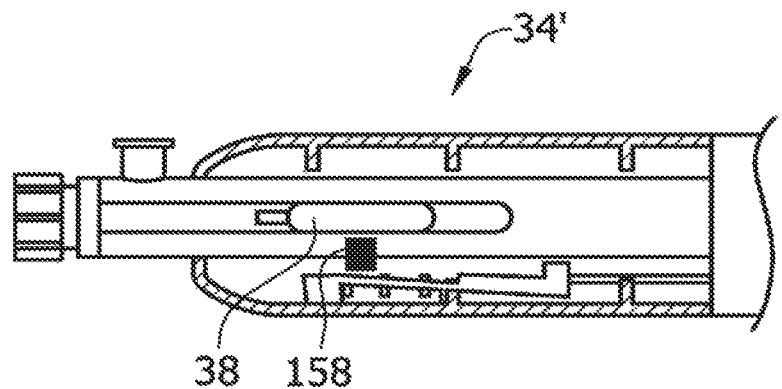
FIG. 25 illustrates a neutral position of a lever of the handle, including a locking device in its non-actuated position.
Figure 26:
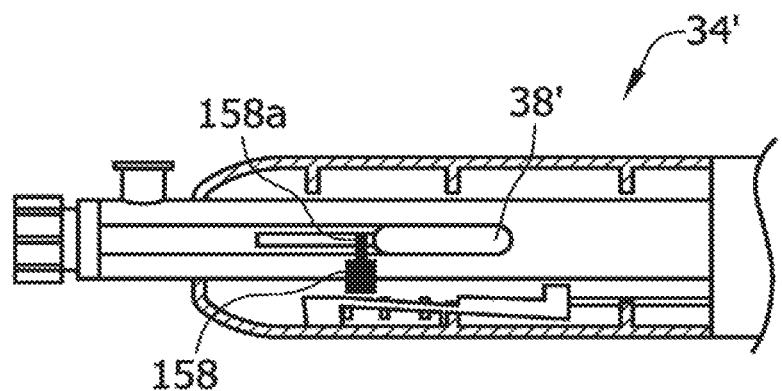
FIG. 26 illustrates a tissue-removing position of the lever of the handle, including a locking device in its non-actuated position.
Figure 27:
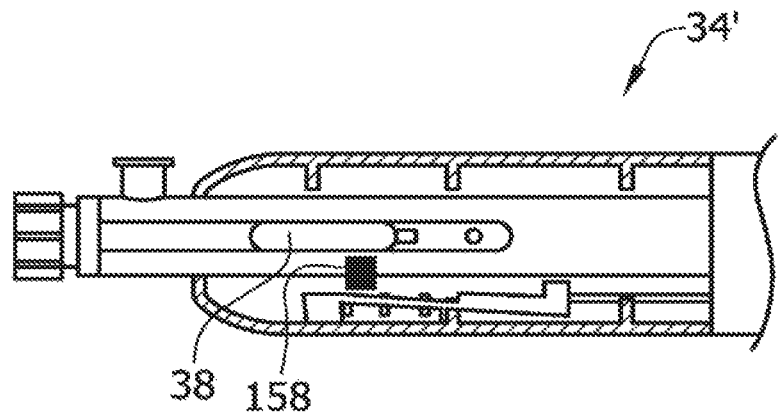
FIG. 27 illustrates a packing position of the lever of the handle, including a locking device in its actuated position.

Referring to FIGS. 21 and 24, the locking control mechanism 150 may include an indicator 170 (e.g., an LED) for communicating to the user that the locking control circuit 154 determined that the cutter 28 has engaged an obstruction and/or the locking control circuit is inhibiting movement of the cutter 28 to its neutral position. In one example, shown in FIG. 27, the indicator 170 is an LED on the handle 34' that is activated by the locking control circuit 154. In another example, the indicator 170 may include a device that provides tactile, audible or some other feedback to the user.

Figure 23:
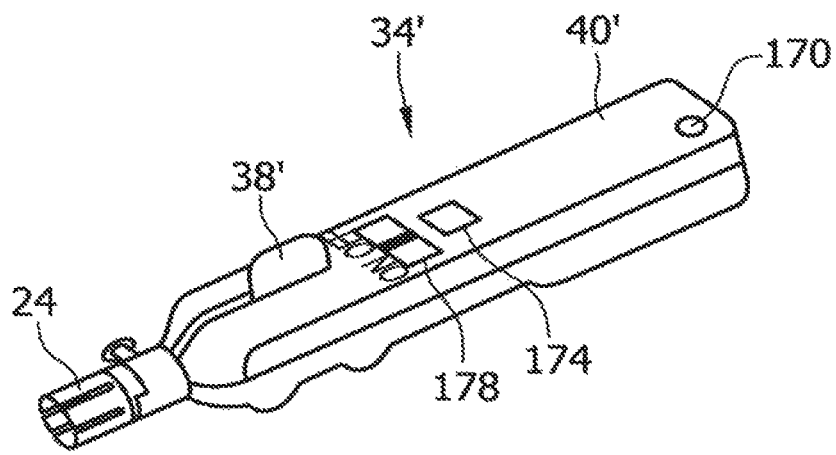
FIG. 23 is a perspective of a second embodiment of the handle for the tissue-removing catheter, including the second embodiment of the operational control mechanism.

The locking control mechanism 150 may include a reset input device 174 (FIG. 23) for resetting the locking control mechanism after the locking control circuit 154 has restricted movement of the cutter 28. The reset input mechanism 174 may comprise a manual switch or button (as shown in FIG. 23) on the handle 34' or may comprise an automatic reset contained within the locking control circuit 150. It is envisioned that after the locking control circuit 154 restricts movement of the cutter 28 and/or after the user becomes aware of such actions such as through the indicator 170, the user will take necessary steps to assess the circumstances surrounding the locking control circuit determining an obstruction and/or prevent further the cutter 28 from further engaging the obstruction. After making the assessment, the user may reset the locking control mechanism 150, and resume treatment.

In this same example, the operational control function of the locking control mechanism 150, as described above herein, may be selectively activated and/or deactivated by the user. For example, if a stent or other implanted structure is not present in the target body lumen (or at least it is not believed that a stent is present), the user can deactivate the locking control mechanism 150 to prevent actuation of the locking device 158 if the cutter 28 engages a hardened tissue (e.g., calcified plaque). It is envisioned that in some cases, the motor 74' may draw power that is at or above the threshold power level when the cutter 28 engages hardened tissue. Thus, if the operational control function of the locking control mechanism 150 is activated, the locking control circuit 154 may inhibit axial movement of the cutter 28 when the cutter engages hardened tissue and prevent parting off and packing of the removed tissue in the tip 42, which may be undesirable. Referring to FIG. 23, in one example, the handle 34' may include a switch 178 (or other input mechanism) for selectively deactivating or activating the locking control mechanism 150.

Figure 22:
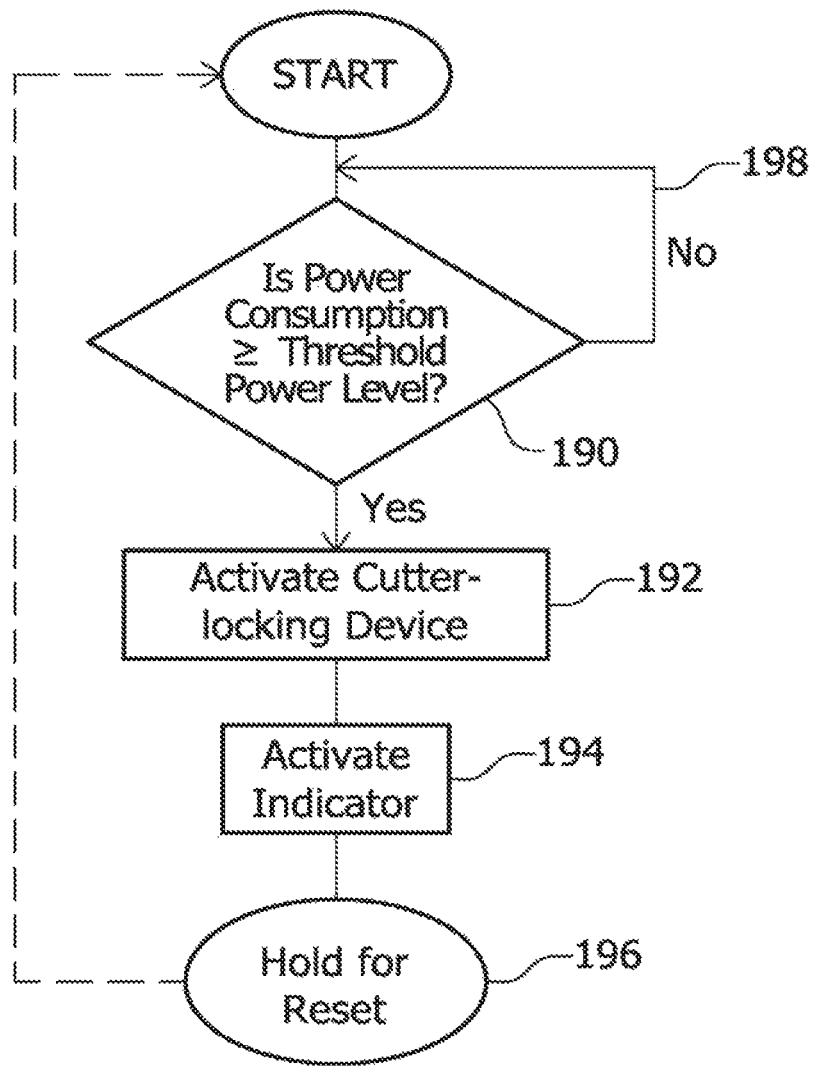
FIG. 22 is an exemplary flow diagram for a locking control circuit of the second embodiment of the operational control mechanism.

An exemplary flow diagram for the locking control circuit 154 is shown in FIG. 22. When the operational control function of the locking control mechanism 150 is active, the locking control circuit 154, at step 190, determines, based on the signal from the sensor 152 and during the cutting operation of the catheter, whether the electrical power being drawn by the electric motor 74' is at least one of equal to and greater than a predetermined threshold power level. The predetermined threshold power level is indicative of the cutter 28 engaging a non-tissue obstruction. If the locking control circuit 154 determines that the electrical power being drawn by the electric motor 74' is at least one of equal to and greater than a predetermined threshold power level, then at step 192 the locking control circuit actuates the locking device 158 to inhibit movement of the cutter 28 from its tissue-removing position to its neutral position. At step 194, the locking control circuit 154 activates the indicator 170 to communicate to the user that a non-tissue obstruction has been detected and the cutter 28 is being locked to inhibit parting off. The inability of the user to move the cutter 28 is continued until (or unless) a reset is activated (such as by a user activating the reset button 174), at step 196. If the locking control circuit 154 determines that the electrical power being drawn by the electric motor 74' is not at least one of equal to and greater than a predetermined threshold power level, then detection of electrical power consumption by the motor is continued at step 198, which may include a delay. It is understood that the steps involved in determining that the cutter 28 is engaging an obstruction and subsequently restricting movement of the cutter may be other than described above. Moreover, these steps may be performed using analog and/or digital circuits, without the use of a microcontroller.

Figure 28:
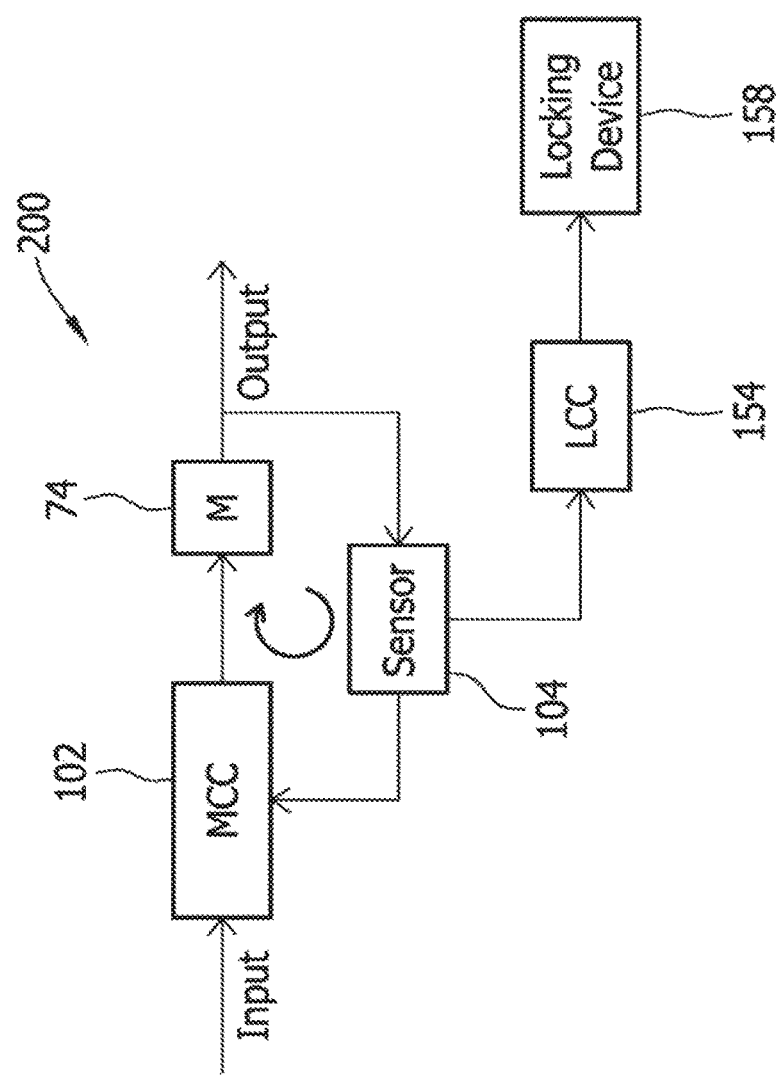
FIG. 28 is an exemplary block diagram of a third embodiment of the operational control mechanism.
Figure 29:
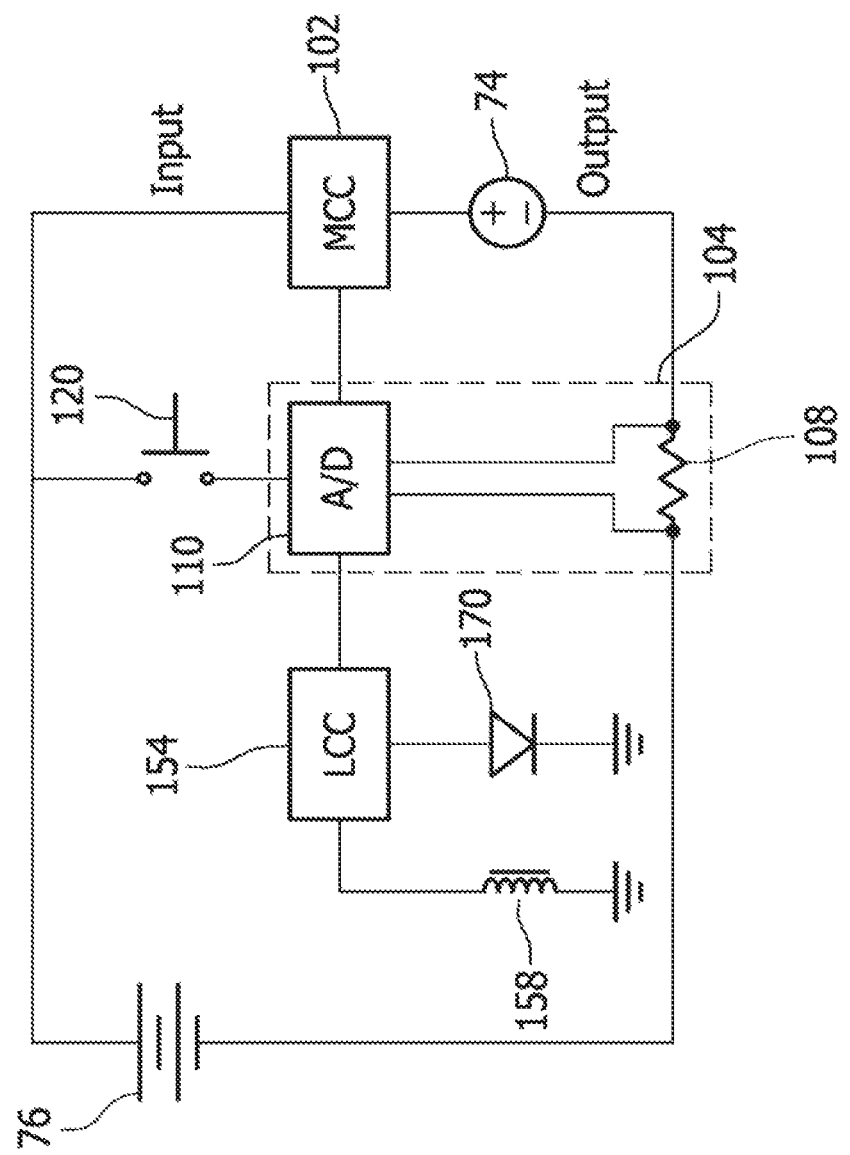
FIG. 29 is an exemplary schematic of the third embodiment of the operational control mechanism.

Referring to FIGS. 28 and 29, in a third embodiment, an operational control mechanism comprises both the motor control mechanism 100 and the locking control mechanism 150. Diagrams of one example of this combined control mechanism, including the motor 74, are indicated generally by reference numeral 200 in FIGS. 28 and 29. The components of the motor control mechanism 100 and the locking control mechanism 150 may be the same as set forth above with respect to the respective embodiments. In this embodiment, the motor control mechanism 100 and the locking control mechanism 150 share a common sensor 104. It is understood that the motor control mechanism 100 and the locking control mechanism 150 may also share a common motor/locking control circuit that is configured to perform the respective operational functions of the control circuits, or the motor and locking control circuits may be separate components, as illustrated.

Referring to FIGS. 30-34, in a fourth embodiment, an operational control mechanism comprises a motor control mechanism 250, which, unlike the first motor control mechanism 100, functions to increase power supplied to the motor 74" a predetermined amount if the motor control mechanism detects that the motor is drawing power (e.g., current) from the power source 76" that is at or above a threshold level (e.g., threshold amperage). In such an example, this predetermined threshold power level would be indicative of the cutter 28 engaging calcified tissue or other hardened tissue in the body lumen. An exemplary handle in which the motor control mechanism of this embodiment may be housed is indicated generally at 34" in FIGS. 33 and 34. The following components of the handle 34" may be similar or identical to the corresponding components of the first handle 34: a housing 40"; a lever 38" (broadly, an actuator); a motor 74"; and a power source 76". Other components of the present handle 34", including the motor control mechanism 250 of this embodiment, are described herein below. Moreover, the present handle 34" may be used with the same catheter 20 described above herein, and therefore, components of the catheter will be indicated by the same reference numbers set forth above.

Figure 30:
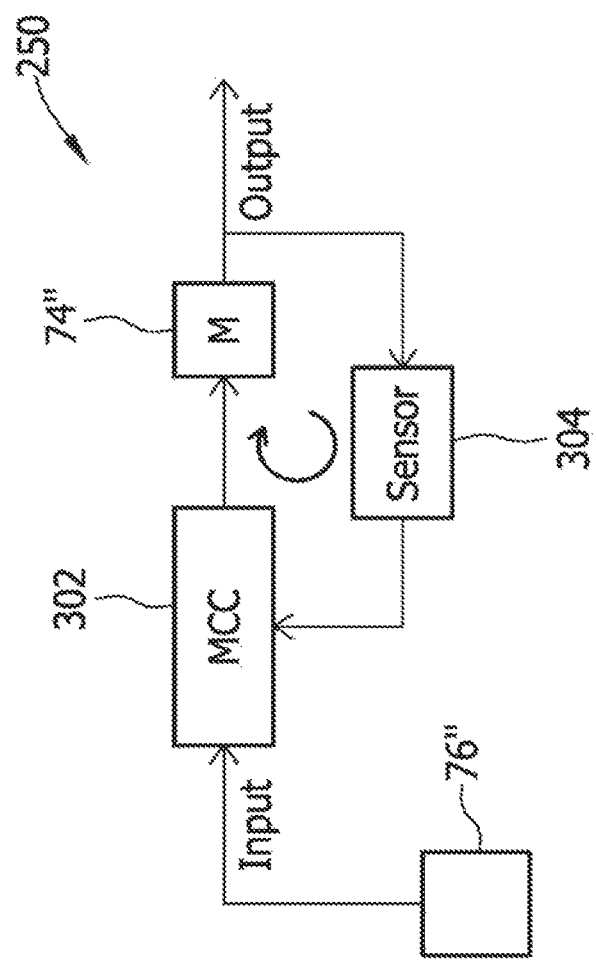
FIG. 30 is an exemplary block diagram of a fourth embodiment of the operational control mechanism.

As shown in FIG. 30, the motor control mechanism 250 includes a motor control circuit 302 that receives electrical current (broadly, electrical power) from the power source 76". The motor control circuit 302 regulates the amount of current that is supplied to the motor 74". The motor control mechanism 250 also includes a sensor 304 that senses a parameter of the motor 74" that is indicative of the amount of electrical power being drawn by the motor at some instantaneous time. The sensor 304 communicates with the motor control circuit 302. The motor control circuit 302 regulates the amount of power supplied to the motor 74" based on the signal it receives from the sensor 304 indicative of the amount of electrical power being drawn by the motor 74" at some instantaneous time. As such, the motor control circuit 250 comprises a feedback loop.

Figure 31:
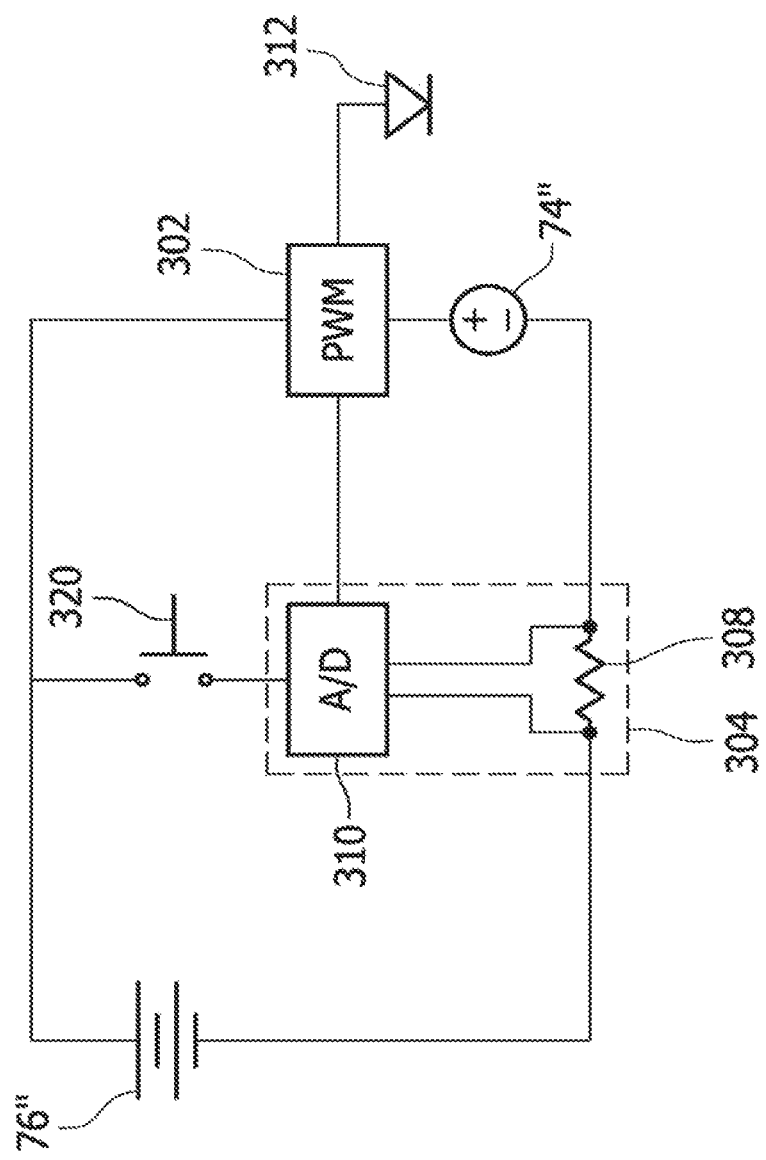
FIG. 31 is an exemplary schematic of the fourth embodiment of the operational control mechanism.

In one non-limiting example illustrated in FIG. 31, the motor control circuit 302 comprises a pulse width modulation (PWM) circuit. For example, the PWM circuit 302 may comprise a microcontroller (not shown) that is programmed to regulate the amount of power supplied to the motor 74" by outputting a duty cycle signal to the motor based on the signal received from the sensor 304. It is understood that the motor control circuit 302 may comprise other types of devices without departing from the scope of the present invention. In the same illustrated example (or another example), the sensor 304 comprises a current sensing resistor 308 and an analog-to-digital (A/D) converter 310 in communication with the current sensing resistor. The A/D converter 310 detects the voltage drop across the current sensing resistor 308, which is indicative of the amount of power being drawn by the motor 74" at some instantaneous time. The analog input is converted to a digital signal by the A/D converter 310. This digital signal is inputted to the PWM circuit 302 (or other motor control circuit). The PWM circuit 302 outputs a duty cycle to the motor 74" based, at least in part, on this digital signal. It is understood that the sensor 304 may be of other types and configurations without departing from the scope of the present invention. It is also understood that the motor control circuit 250, which is configured to detect a parameter of the motor and increase power supplied to the motor, may be of other configurations, other than illustrated and described above, without departing from the scope of the present invention.

The motor control circuit 302 is configured to increase the power supplied to the motor 74" if the motor control circuit determines that the motor is drawing power (e.g., current) that is at or above a predetermined threshold power level (e.g., threshold amperage). In such an example, this predetermined threshold power level would be indicative of the cutter 28 engaging hardened tissue. The motor control circuit 302 increases power supplied to the motor 74" to enable the cutter 28 to cut through the hardened tissue. In one non-limiting example, where the motor control circuit 302 includes a PWM circuit, the PWM circuit may increase the duty cycle about 10% to 100% or more from its original duty cycle.

Figure 33:
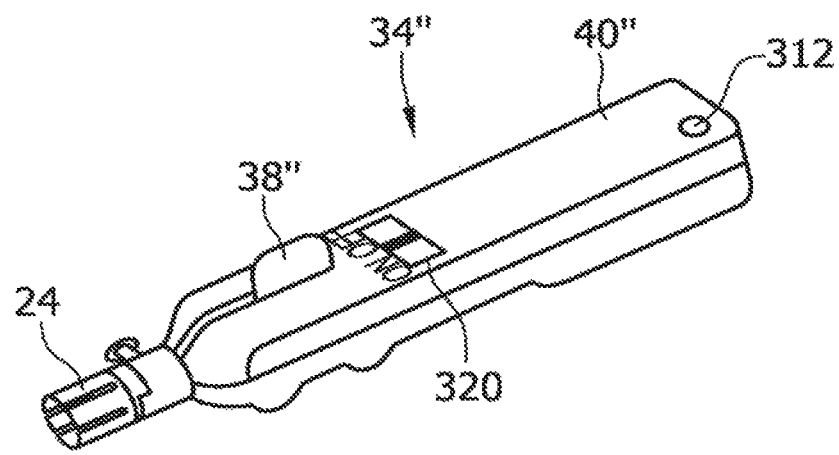
FIG. 33 is a perspective of a third embodiment of the handle for the tissue-removing catheter, including the fourth embodiment of the operational control mechanism.
Figure 34:
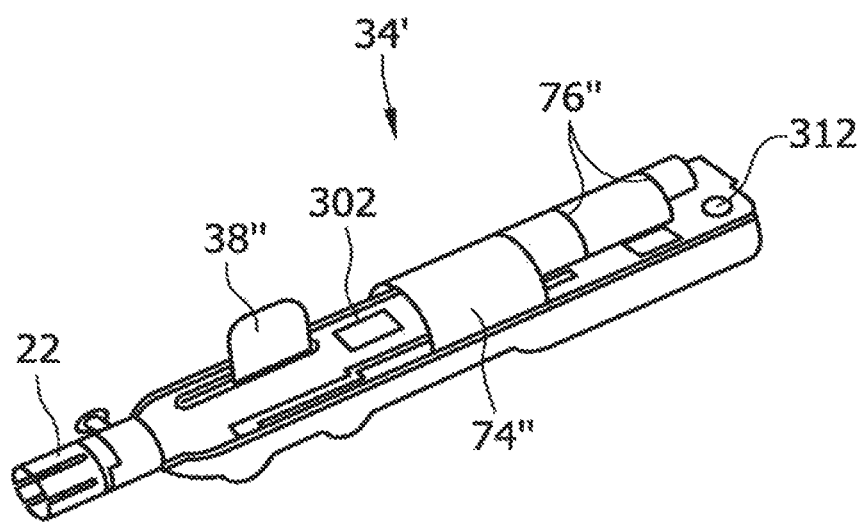
FIG. 34 is similar to FIG. 33, with a cover of the handle removed.

Referring to FIGS. 33 and 34, the handle 34" may include an indicator 312 (e.g., an LED) for communicating to the user that the motor control circuit 302 detected that the cutter 28 has engaged a hardened tissue obstruction and is (or has) increasing the power supplied to the motor 74". In one example, shown in FIG. 24, the indicator 312 (e.g., LED) is activated by the motor control circuit 302 (e.g., a microcontroller). In another example, the indicator 312 may include be a device that provides tactile or audible feedback to the user.

In this same example, the handle 34" may be configured to allow a user to selectively activate and deactivate the motor control mechanism 250. For example, if there is a stent or other implanted structure in the target body lumen (e.g., artery), the user can deactivate the motor control unit 250 to prevent the motor control circuit 302 from increasing power to the motor 74" if the cutter 28 engages the stent or other implanted structure. It is envisioned that in some cases, the motor 74" may draw power that is at or above the threshold power level when the cutter 28 engages the stent or other implanted structure. Thus, if the motor control mechanism 250 is activated, the motor control circuit 302 may increase power to the motor 74", and thus, the speed of the motor 74" when the cutter 28 engages the stent or other implanted structure, which could cause entanglement with the stent or other implanted structure and negatively impact treatment. In one example, the handle 34" may include a switch 320 (or other input mechanism) for selectively deactivating or activating the motor control circuit 250.

Figure 32:
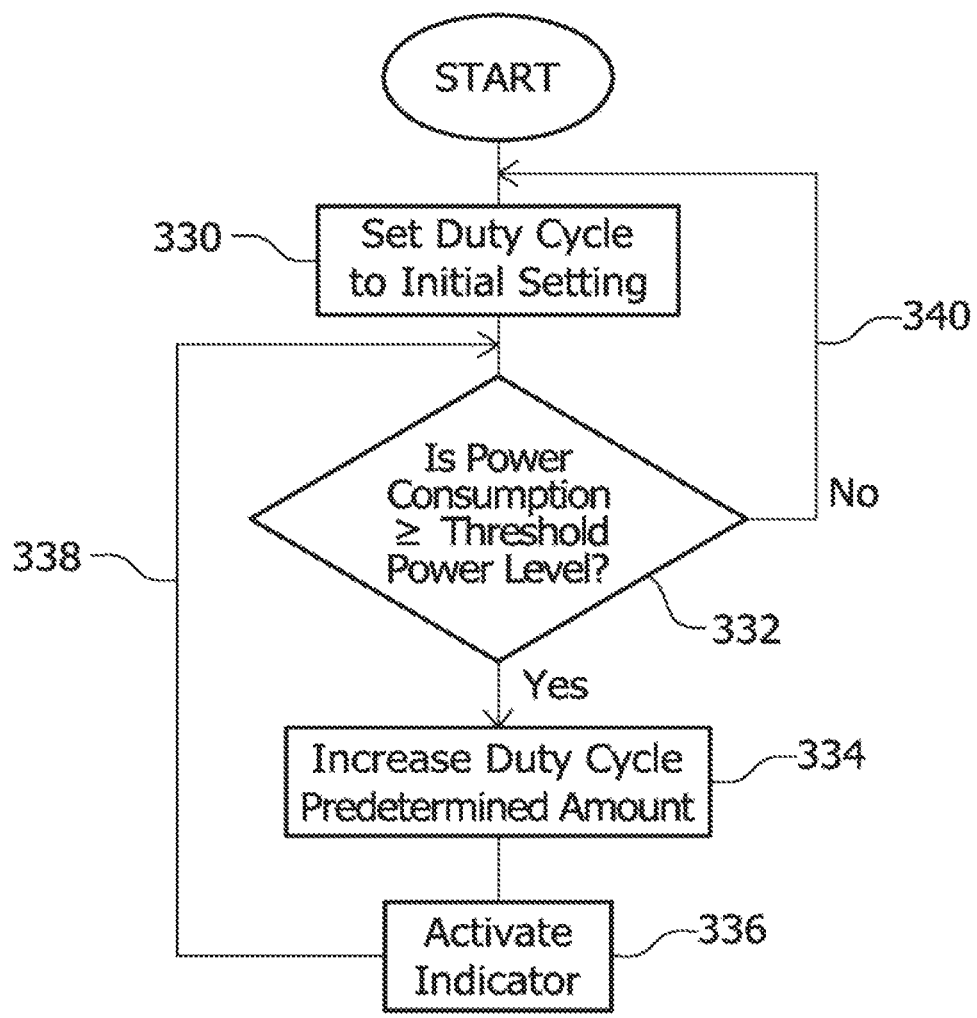
FIG. 32 is an exemplary flow diagram for a motor control circuit of the fourth embodiment of the operational control mechanism.

An exemplary flow diagram for the motor control circuit 302 is shown in FIG. 32. In this example, the motor control circuit 302 includes a PWM circuit, which includes a microcontroller for regulating the duty cycle supplied to the motor 74". When the motor control mechanism 250 is active (e.g., such as by using the switch 320), the microcontroller sets the duty cycle to an initial duty cycle at step 330. At step 332, the microcontroller determines, based on the data from the sensor 304 and during the cutting operation of the catheter 20, whether the electrical power being drawn by the electric motor 74" is at least one of equal to and greater than a predetermined threshold power level. The predetermined threshold power lever is indicative of the cutter 28 engaging a hardened tissue obstruction. If the microcontroller determines that the electrical power being drawn by the electric motor 74" is not at least one of equal to and greater than a predetermined threshold power level, then detection of electrical power consumption by the motor is continued at step 340, which may include a delay.

If, however, the microcontroller determines that the electrical power being drawn by the electric motor 74" is at least one of equal to and greater than a predetermined threshold power level, then at step 334 the microcontroller increases the amount of power supplied to the motor 74" (i.e., increases the duty cycle). At step 336, the microcontroller activates the indicator 312 to communicate to the user that a hardened tissue obstruction has been detected and that the power supplied to the motor 74" is being (or has been) increased. As shown at step 338, this increase of power supplied to the motor 74" is continued until (or unless) the microcontroller subsequently determines that the electrical power being drawn by the electric motor 74" is at least one of equal to and less than the predetermined threshold power level, at which time, the microcontroller may reset the duty cycle to the initial setting (as shown) or reduce the duty cycle by a predetermined amount, until a suitable power level is reached. It is understood that the steps involved in determining that the cutter 28 is engaging an obstruction and subsequently increasing power supplied to the motor 74" may be other than described above. Moreover, these steps may be performed using analog and/or digital circuits, without the use of a microcontroller.

It is also contemplated that the catheter 20 may include the first embodiment of the motor control mechanism 100 (and/or the locking control mechanism 150) and the second embodiment of the motor control mechanism 250. In such an embodiment, the catheter may be configured such that the user can selectively activate one of the first and second embodiments of the motor control mechanisms 100, 250, respectively, during the cutting operation (or a portion thereof), or the user can selectively deactivate both of the first and second embodiments of the motor control mechanisms. In one example, a single handle (not shown) may include each motor control mechanism 100, 250.

Referring to FIGS. 30-34, in a fourth embodiment, an operational control mechanism comprises a locking control mechanism 350, different from the first locking control mechanism 150, which functions to inhibit the user from moving the cutter 28 from its packing position (FIG. 5B) back to its tissue-removing position (FIG. 4B) if the locking control mechanism detects that the collection chamber 53 in the tip member 42 is full and should be emptied before proceeding with additional cutting. An exemplary handle in which this locking control mechanism 350 may be housed is indicated generally at 34''' in FIGS. 35-39. The following components of the handle 34''' may be similar or identical to the corresponding components of the first handle 34: a housing 40'''; a lever 38''' (broadly, an actuator); a motor 74'''; and a power source 76'''. Other components of the present handle 34''', including the locking control mechanism 350, are described herein below. Moreover, the present handle 34''' may be used with the same catheter 20 described above herein, and therefore, components of the catheter will be indicated by the same reference numbers set forth above.

Figure 37:
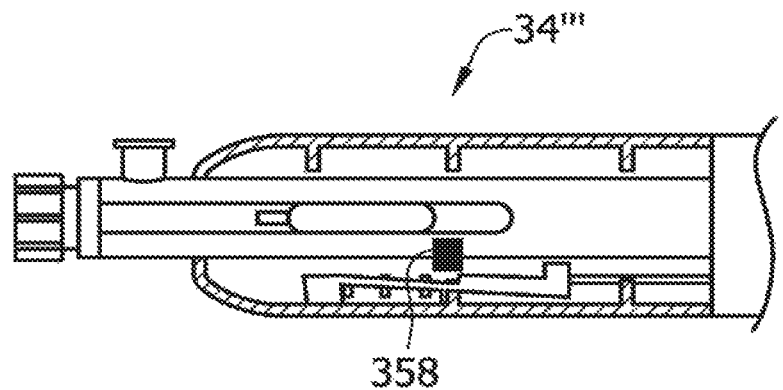
FIG. 37 illustrates a neutral position of a lever of the handle, including a locking device in its non-actuated position.
Figure 38:
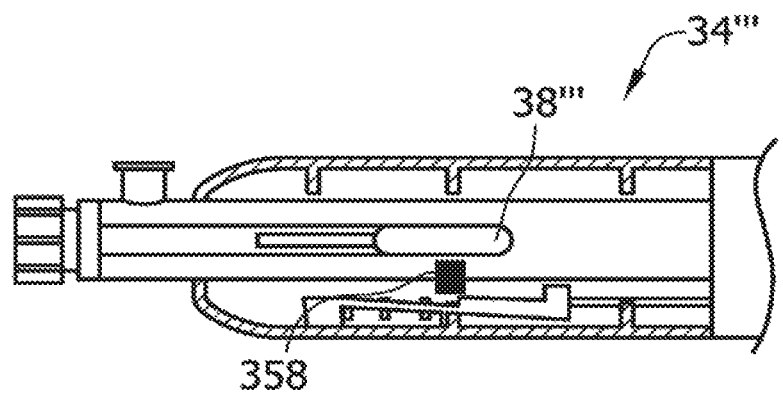
FIG. 38 illustrates a tissue-removing position of the lever of the handle, including a locking device in its non-actuated position.
Figure 39:
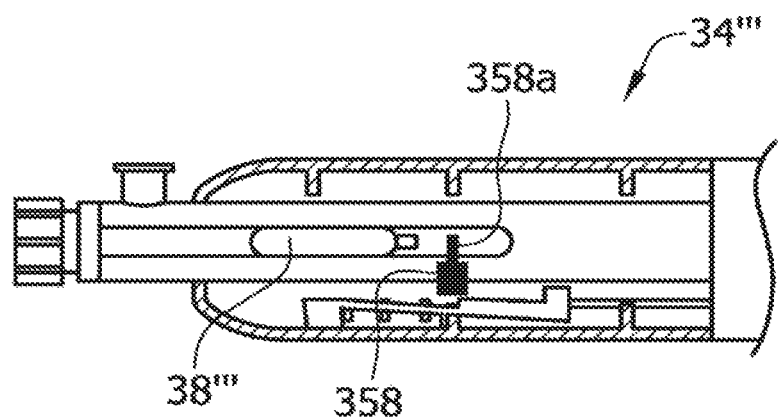
FIG. 39 illustrates a packing position of the lever of the handle, including a locking device in its actuated position.
Figure 40:
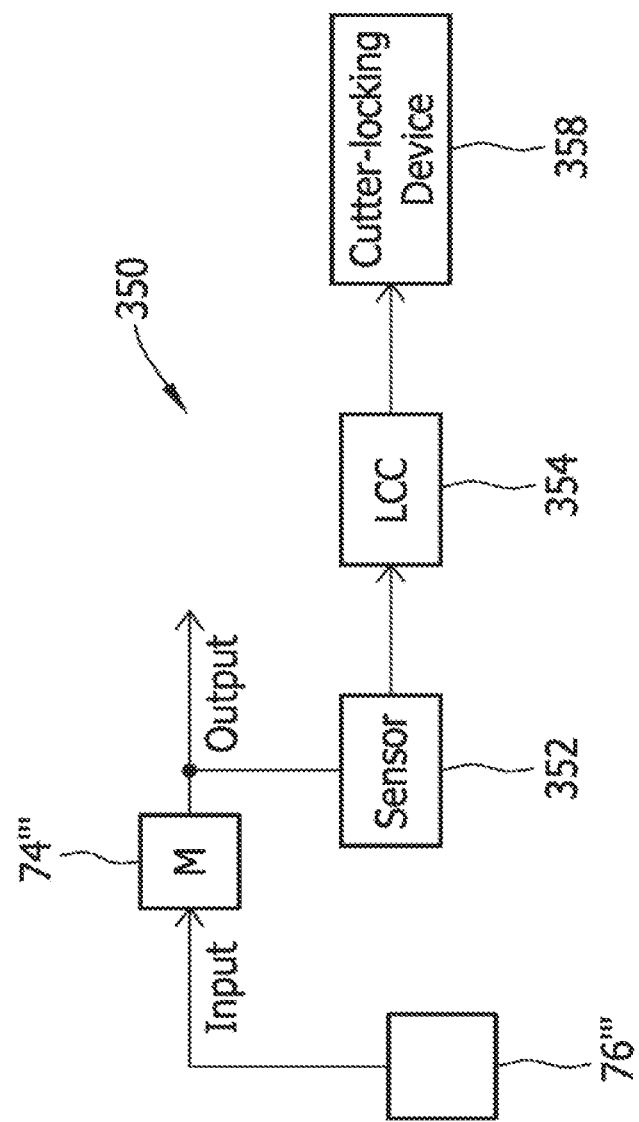
FIG. 40 is an exemplary block diagram of the fifth embodiment of the operational control mechanism.

A block diagram of one example of the locking control mechanism 350, including the motor 74''', is illustrated in FIG. 40. The locking control mechanism 350 includes a sensor 352, which may be identical or similar to the sensor 152 in the locking control mechanism 150, and a locking control circuit 354 in communication with the sensor. The locking control circuit 354 is in communication with and actuates a locking device 358. The locking device 358 is selectively configurable between a locked configuration (FIG. 39), in which the locking device inhibits movement of the cutter 28 from its packing position to its tissue-removing position, and an unlocked configuration (FIGS. 37 and 38), in which the locking device allows movement of the cutter from its packing position to its tissue-removing position. In one example, the locking device 358 comprises an electromechanical solenoid (or other device). When the solenoid 358 is configured in its locked configuration, it inhibits movements of the lever 38''' from its tissue-removing position to its neutral position. As shown in FIGS. 37-39, the locking solenoid 358 is positioned adjacent the lever 38''', such that when activated by the locking control circuit 354, an armature 358a of the electromechanical solenoid blocks the path of the lever to inhibit the lever from moving to its neutral position (FIG. 39).

During normal operation, the locking device 358 is in its unlocked configuration. Unlike the previous embodiments, the motor 74''' continues to drive the cutter 28 when the cutter is in its packing position (i.e., at least a partial duty cycle is supplied to the motor to drive the cutter in its packing position). When the cutter 28 is in the packing position, the locking control circuit 354 receives a signal from the sensor 352 that is indicative of the power being drawn by the motor 74''' and determines whether the power being drawn by the motor is at or above a predetermined threshold power level. Power being drawn by the motor 74''' at or above the predetermined threshold power level is indicative of the collection chamber 53 being full. If it is determined that power being drawn by the motor 74''' at or above the predetermined threshold power level, then the locking control circuit 354 configures the locking device 358 to its locked configuration to inhibit movement of the cutter 28 from its packing position to its tissue-removing position. By restricting movement of the cutter 28 from its packing position to its tissue-removing position after determining that the collection chamber 53 is full, the locking control circuit 354 inhibits the user from removing additional tissue without first emptying the collection chamber.

Figure 41:
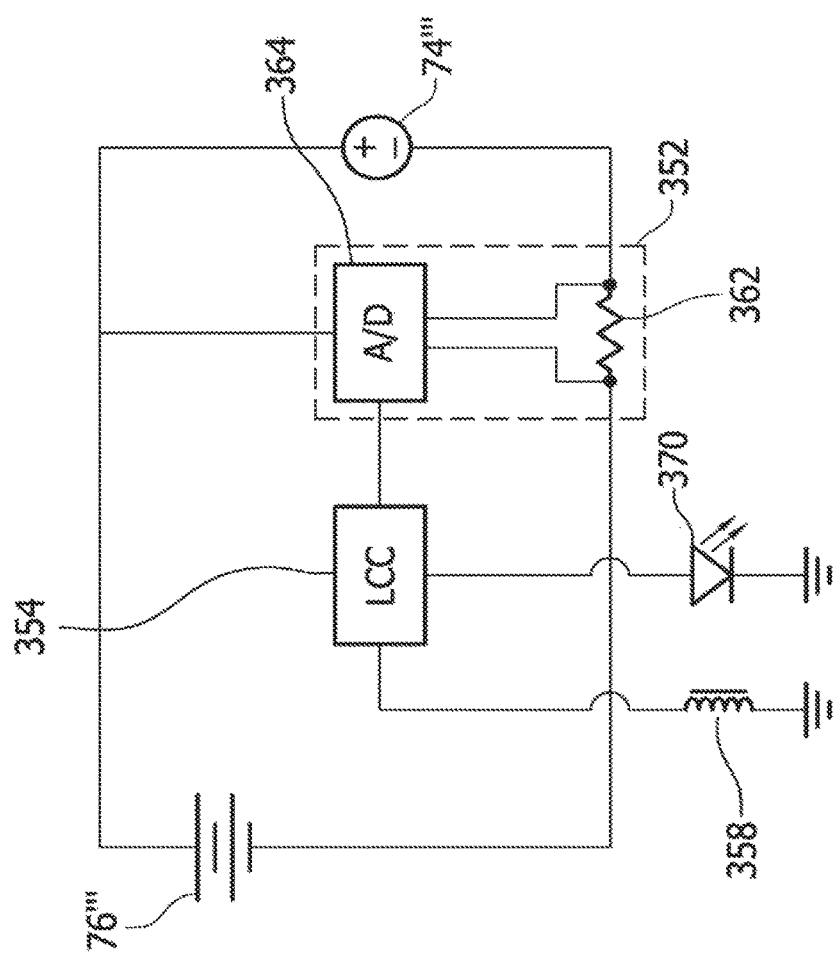
FIG. 41 is an exemplary schematic of the fifth embodiment of the operational control mechanism.
Figure 42:
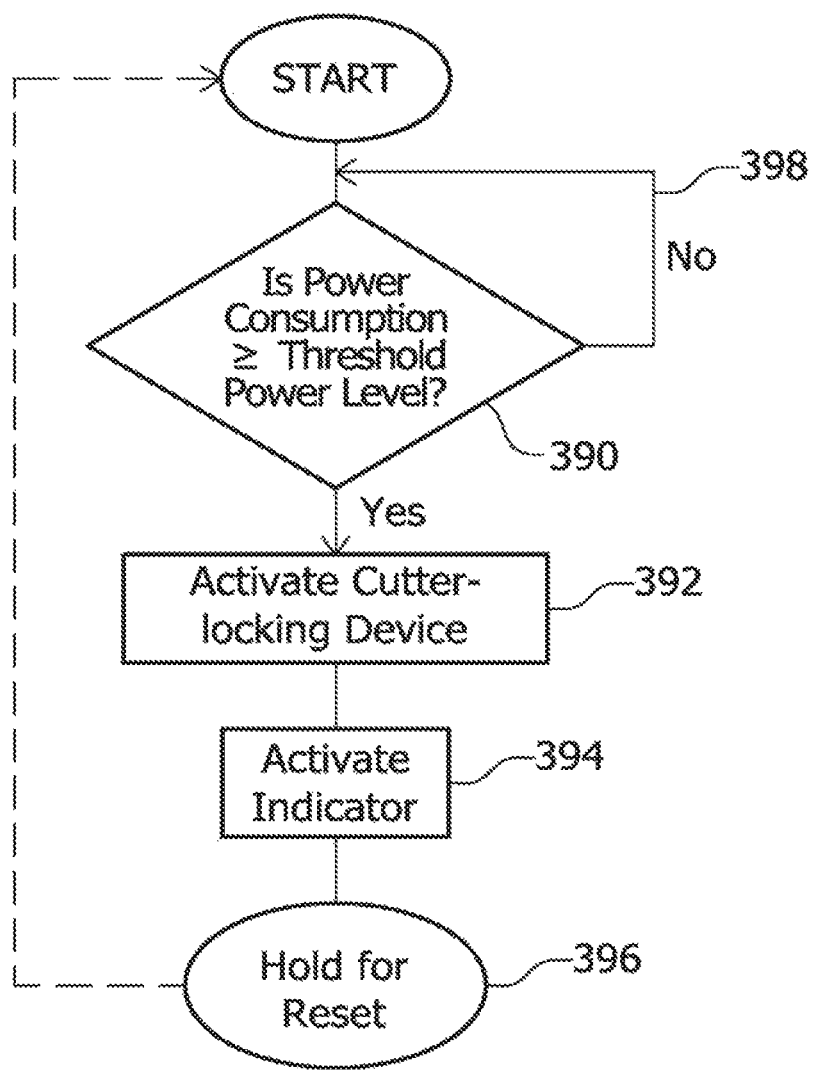
FIG. 42 is an exemplary flow diagram for a locking control circuit of the fifth embodiment of the operational control mechanism.

In one non-limiting example illustrated in FIG. 41, the locking control circuit 354 may be similar, if not identical, to the locking control circuit 154 of the second embodiment. The sensor 352 of the locking control mechanism 350 includes a current sensing resistor 362 and an analog-to-digital (A/D) converter 364 in communication with the current sensing resistor. Like the first embodiment illustrated in FIG. 18, the present A/D converter 364 detects the voltage drop across the current sensing resistor 362, which is indicative of the amount of power being consumed (i.e., drawn) by the motor 74''' at some instantaneous time. The analog input is converted to a digital signal by the A/D converter 364. This digital signal is inputted to the locking control circuit 354 (e.g., a microcontroller). If the locking control circuit 354 determines that the power being drawn by the motor 74''' is at or above the predetermined threshold power level, then the locking control circuit 354 may actuate the locking device 358 to configure the locking device in its locked configuration. It is understood that the locking control mechanism 350, which is configured to detect an operating parameter of the motor 74''' and restrict movement of the cutter 28, may be of other configurations, other than illustrated and described above, without departing from the scope of the present invention.

Figure 35:
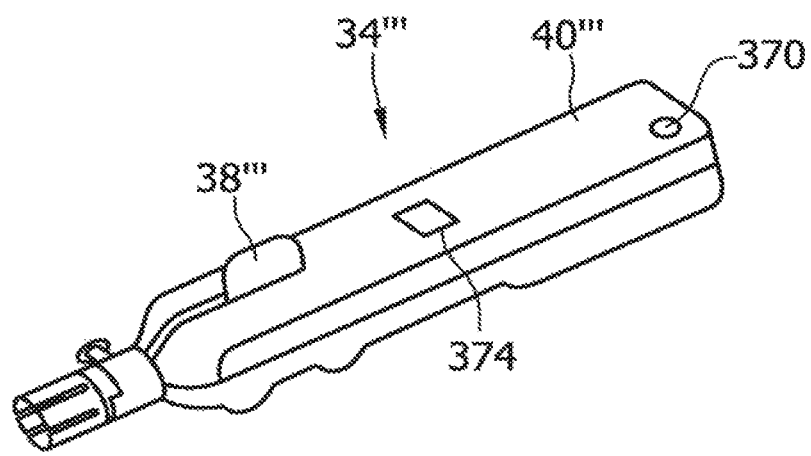
FIG. 35 is a perspective of a fourth embodiment of the handle for the tissue-removing catheter, including a fifth embodiment of the operational control mechanism.
Figure 36:
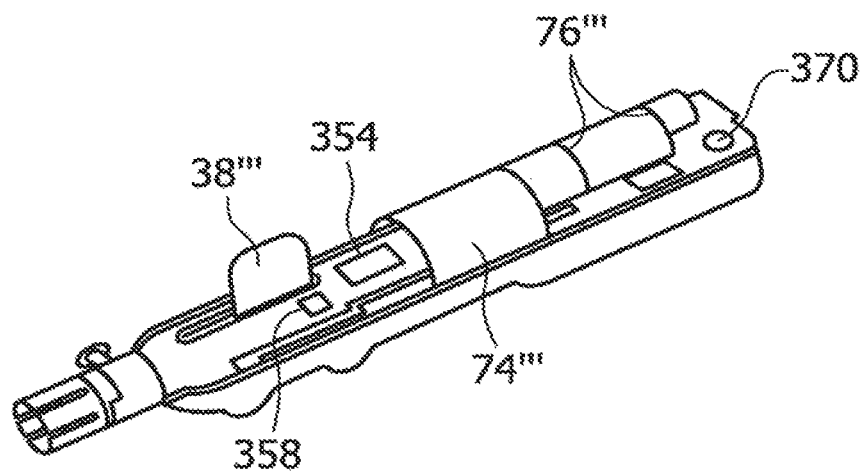
FIG. 36 is similar to FIG. 35, with a cover of the handle removed.

Referring to FIGS. 35 and 41, the locking control mechanism 350 may include an indicator 370 (e.g., an LED) for communicating to the user that the locking control circuit 354 determined that the collection chamber 53 needs to be emptied and/or the locking control circuit is inhibiting movement of the cutter 28 to its tissue-removing position. In one example, shown in FIG. 41, the indicator 370 is an LED on the handle 34''' that is activated by the locking control circuit 354. In another example, the indicator 370 may include a device that provides tactile, audible or some other feedback to the user.

The locking control mechanism 350 may include a reset input device 374 (FIG. 35) for resetting the locking control mechanism after the locking control circuit 354 has restricted movement of the cutter 28. The reset input mechanism 374 may comprise a manual switch or button (as shown in FIG. 35) on the handle 34' or may comprise an automatic reset contained within the locking control mechanism 350. It is envisioned that after the locking control circuit 354 restricts movement of the cutter 28 and/or after the user becomes aware of such actions, such as through the indicator 370, the user will withdraw the catheter 20 from the body lumen BL, reset the locking control mechanism 350, empty the collection chamber 53, and then reinsert the catheter into the body lumen to resume treatment.

An exemplary flow diagram for the locking control circuit 354 is shown in FIG. 41. When the operational control function of the locking control mechanism 350 is active, the locking control circuit 354, at step 390, determines, based on the signal from the sensor 352 and during packing of removed tissue in the collection chamber 53, whether the electrical power being drawn by the electric motor 74''' is at least one of equal to and greater than a predetermined threshold power level. The predetermined threshold power level is indicative of the collection chamber 53 being full of removed tissue. If the locking control circuit 354 determines that the electrical power being drawn by the electric motor 74''' is at least one of equal to and greater than a predetermined threshold power level, then at step 392 the locking control circuit actuates the locking device 358 to inhibit movement of the cutter 28 from its packing position to its tissue-removing position. At step 394, the locking control circuit 354 activates the indicator 370 to communicate to the user that a non-tissue obstruction has been detected and the cutter 28 is being locked because the collection chamber 53 is full. The inability of the user to move the cutter 28 is continued until (or unless) a reset is activated (such as by a user activating the reset button 374), at step 396, preferably after the catheter 20 has been withdrawn and the collection chamber 53 has been emptied. If the locking control circuit 354 determines that the electrical power being drawn by the electric motor 74''' is not at least one of equal to and greater than a predetermined threshold power level, then detection of electrical power consumption by the motor is continued at step 398, which may include a delay. It is understood that the steps involved in determining that the cutter 28 is engaging an obstruction and subsequently restricting movement of the cutter may be other than described above. Moreover, these steps may be performed using analog and/or digital circuits, without the use of a microcontroller.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Having described the invention in detail, it will be apparent that modifications and variations are possible without departing from the scope of the invention defined in the appended claims. When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a body lumen during a cutting operation thereof, the tissue-removing catheter comprising:
    an elongate catheter body configured for insertion into the body lumen, the catheter body having opposite distal and proximal portions, and a longitudinal axis extending between the distal and proximal portions;
    a tissue-removing element located generally at the distal portion of the catheter body for rotation generally about the longitudinal axis of the catheter body;
    a deployment mechanism operably connected to the tissue-removing element, the deployment mechanism configured to move the tissue-removing element between a tissue-removing position, in which the tissue-removing element is exposed through the distal portion of the catheter body and capable of performing the cutting operation, and a neutral position, in which the tissue-removing element is positioned inside the distal portion of the catheter body;
    an electric motor operably connected to the tissue-removing element for imparting rotation of the tissue-removing element about a rotational axis during the cutting operation of the catheter;
    a locking device selectively configurable between a locked configuration, in which the locking device inhibits movement of the tissue-removing element from its tissue-removing position to its neutral position, and an unlocked configuration, in which the locking device allows movement of the tissue-removing element from its tissue-removing position to its neutral position;
    a sensor configured to detect a parameter of the electric motor during the cutting operation of the catheter when the tissue-removing element is in its tissue-removing position;
    a locking control circuit in electrical communication with the sensor and the locking device, wherein during an operational control function, the locking control circuit is configured to:
    receive a signal from the sensor based at least in part on the parameter of the electric motor detected during the cutting operation of the catheter,
    determine whether the received signal is indicative of the tissue-removing element engaging a non-tissue obstruction, and
    configure the locking device in its locked configuration to inhibit movement of the tissue-removing element from its tissue-removing position to its neutral position if the received signal is indicative of the tissue-removing element engaging a non-tissue obstruction.

2. The tissue-removing catheter set forth in claim 1, wherein the parameter detectable by the sensor is indicative of the amount of electrical power being drawn by the electric motor.

3. The tissue-removing catheter set forth in claim 2, wherein the sensor includes a current sensing resistor.

4. The tissue-removing catheter set forth in claim 3, further comprising an indicator in electrical communication with the locking control circuit, wherein the locking control circuit is configured to activate the indicator if the electrical power being drawn by the electric motor is determined to be at least one of equal to and greater than the predetermined threshold power level.

5. The tissue-removing catheter set forth in claim 2, further comprising a handle connected to the proximal portion of the catheter body, wherein the locking control circuit, the motor, and the locking device are disposed in the handle.

6. The tissue-removing catheter set forth in claim 5, further comprising a source of power disposed in the handle, wherein the parameter detectable by the sensor is indicative of the amount of electrical power being drawn from the source of power by the electric motor.

7. The tissue-removing catheter set forth in claim 5, wherein the deployment mechanism comprises a manual actuator on the handle, wherein the manual actuator is selectively movable relative to the handle between a first position for positioning the tissue-removing element in the tissue-removing position, and a second position for positioning the tissue-removing element in the neutral position, the locking device being configured to inhibit the manual actuator from being moved from the first position to the second position when the locking device is in its locked position.

8. The tissue-removing catheter set forth in claim 7, wherein the locking device comprises an electromechanical solenoid disposed generally adjacent to the manual actuator.

9. The tissue-removing catheter set forth in claim 2, further comprising a motor control circuit, wherein the motor control circuit is configured to determine if the electrical power being drawn by the electric motor is at least one of equal to and greater than a predetermined threshold power level, wherein the motor control circuit is configured to perform at least one of the following, when the electrical power being drawn by the electric motor is determined to be at least one of equal to and greater than the predetermined threshold power level:
    reduce the amount of electrical power being supplied to the motor, and
    deactivate the motor.

10. The tissue-removing catheter set forth in claim 9, wherein the motor control circuit comprises a pulse width modulation (PWM) circuit configured to reduce the amount of electrical power supplied to the motor when the electrical power being drawn by the electric motor is determined to be at least one of equal to and greater than the predetermined threshold power level.

11. The tissue-removing catheter set forth in claim 9, wherein the motor control circuit comprises a pulse width modulation (PWM) circuit configured to deactivate the motor when the electrical power being drawn by the electric motor is determined to be at least one of equal to and greater than the predetermined threshold power level.

12. The tissue-removing catheter set forth in claim 1, further comprising a switch for at least one of activating and deactivating the operational control function of locking control circuit.

13. A handle for a tissue-removing catheter including a rotatable tissue-removing element, and a deployment mechanism operably connected to the tissue-removing element and configured to move the tissue-removing element between a tissue-removing position, in which the tissue-removing element is exposed through the catheter body and capable of performing the cutting operation, and a neutral position, in which the tissue-removing element is positioned inside the catheter, the handle comprising:
- an electric motor operably connectable to the tissue-removing element for imparting rotation of the tissue-removing element during the cutting operation of the catheter;
- a locking device selectively configurable between a locked configuration, in which the locking device inhibits movement of the tissue-removing element from its tissue-removing position to its neutral position, and an unlocked configuration, in which the locking device allows movement of the tissue-removing element from its tissue-removing position to its neutral position;
- a sensor configured to detect a parameter of the electric motor during the cutting operation of the catheter when the tissue-removing element is in its tissue-removing position;
- a locking control circuit in electrical communication with the sensor and the locking device, wherein during an operational control function, the locking control circuit is configured to:
- receive a signal from the sensor based at least in part on the parameter of the motor detected during the cutting operation of the catheter,
- determine whether the received signal is indicative of the tissue-removing element engaging a non-tissue obstruction, and
- configure the locking device in its locked configuration to inhibit movement of the tissue-removing element from its tissue-removing position to its neutral position if the received signal is indicative of the tissue-removing element engaging a non-tissue obstruction.

14. The handle set forth in claim 13, wherein the parameter detectable by the sensor is indicative of the amount of electrical power being drawn by the electric motor.

15. The handle set forth in claim 14, further comprising a source of power, wherein the parameter detectable by the sensor is indicative of the amount of electrical power being drawn from the source of power by the electric motor.

16. The handle set forth in claim 13, further comprising a manual actuator selectively movable between a first position for positioning the tissue-removing element in the tissue-removing position, and a second position for positioning the tissue-removing element in the neutral position, the locking device being configured to inhibit the manual actuator from being moved from the first position to the second position when the locking device is in its locked position.

17. The handle set forth in claim 16, wherein the locking device comprises an electromechanical solenoid disposed generally adjacent to the manual actuator.

18. The handle set forth in claim 16, further comprising an indicator in electrical communication with the locking control circuit, wherein the locking control circuit is configured to activate the indicator if the electrical power being drawn by the electric motor is determined to be at least one of equal to and greater than the predetermined threshold power level.

19. The handle set forth in claim 16, wherein the locking control circuit is configured to perform at least one of the following, when the electrical power being drawn by the electric motor is determined to be at least one of equal to and greater than the predetermined threshold power level:
- reduce the amount of electrical power being supplied to the motor, and
- deactivate the motor.

20. The handle set forth in claim 13, further comprising a switch for at least one of activating and deactivating the operational control function of locking control circuit.

* * * * *